US007122348B2

(12) United States Patent
Wong, Jr. et al.

(10) Patent No.: US 7,122,348 B2
(45) Date of Patent: Oct. 17, 2006

(54) AAV2 REP PROTEIN FUSIONS

(75) Inventors: Kamehameha Kay-Min Wong, Jr., Sierra Madre, CA (US); Saswati Chatterjee, Sierra Madre, CA (US); Joel Conrad, Claremont, CA (US); Stella Kim, San Diego, CA (US)

(73) Assignee: City of Hope, Duarte, CA (US)

( * ) Notice: Subject to any disclaimer, the term of this patent is extended or adjusted under 35 U.S.C. 154(b) by 146 days.

(21) Appl. No.: 10/732,813

(22) Filed: Dec. 11, 2003

(65) Prior Publication Data

US 2005/0003344 A1 Jan. 6, 2005

Related U.S. Application Data

(60) Provisional application No. 60/432,258, filed on Dec. 11, 2002.

(51) Int. Cl.
*C21P 21/02* (2006.01)
*C07H 17/00* (2006.01)
*C07K 14/00* (2006.01)

(52) U.S. Cl. ................ 435/69.1; 435/320.1; 536/23.1; 530/350

(58) Field of Classification Search ................ 530/350; 536/23.1; 435/69.1, 320.1
See application file for complete search history.

(56) References Cited

U.S. PATENT DOCUMENTS 6,627,617 B1 * 9/2003 Samulski et al. ............. 514/44

OTHER PUBLICATIONS

Antoni et al. 1991. J. Virology 65(1): 396-404.*

Dilber, M.S., et al., "Intercellular delivery of thymidine kinase prodrug activating enzyme by the herpes simplex virus protein, VP22," *Gene Therapy* 6:12-21, 1999.

Elliott, Gillian, and Peter O'Hare, "Intercellular Trafficking and Protein Delivery by a Herpesvirus Structural Protein," *Cell* 88:223-233, Jan. 24, 1997.

Elliott, Gillian, and Peter O'Hare, Intercellular Trafficking of VP22-GFP fusion proteins, *Gene Therapy* 6:149-151, 1999.

Elliott, Gillian, and Peter O'Hare, "Herpes Simplex Virus Type 1 Tegument Protein VP22 Induces the Stabilization and Hyperacetylation of Microtubles," *Journal of Virology* 72(8):6448-6455, Aug. 1998.

Elliott, Gillian, and Peter O'Hare, "Cytoplasm-to-Nucleus Translocation of a Herpesvirus Tegument Protein during Cell Divison," *Journal of Viroloy* 74(5):2131-2141, Mar. 2000.

Fang, B., et al., "Intercellular trafficking of VP22-GFP fusion proteins is not observed in cultured mammalian Cells," *Gene Therapu* 5:1:1420-1424, 1998.

Kotin, Robert M., et al., "Site-specific integration by adeno-associated virus," *Proc. Natl. Acad. Sci. USA* 87:2211-2215, Mar. 1990.

Nagahara, Hikaru, et al., "Transduction of full-length TAT fusion proteins onto mammalian cells: TAT-$p27^{Kip1}$ induces cell migration," *Nature Medicine* 4(12):1449-1452, Dec. 1998.

Phelan, Anne, et al., "Intercellular delivery of functional p53 by the herpesvirus protein VP22," *Nature Biotechnology* 16:440-443, May 1998.

Podsakoff, Greg, et al., "Efficient Gene Transfer into Nondividing Cells by Adeno-Associated Virus-Based Vectors," *Journal of Virology* 68(9):5656-5666, 1994.

Rinaudo, Daniela, et al., "Conditional Site-Specific Integration into Human Chromosone 19 by Using a Ligand-Dependent Chimeric Adeno-Associated Virus/Rep Protein," *Journal of Virology* 74(1):281-294, Jan. 2000.

Samulski, R.J., et al., "Targeted integration of adeno-associated virus (AAV) into human chromosone 19," *The EMBO Journal* 10(12):3941-3950, 1991.

Schwarze, Steven R., et al., "In Vivo Protein Transduction: Delivery of a Biologically Active Protein into the Mouse," *Science* 285:1569-1572, Sep. 3, 1999.

Schwarze, Steven R., and Steven F. Dowdy, "*In vivo* protein transduction: intracellular delivery of biologically active proteins, compounds and DNA," *Trends in Pharmacol. Sci.* 21:45-48, Feb. 2000.

Surosky, Richard T., et al., "Adeno-Associated Virus Rep Proteins Target DNA Sequences to a Unique Locus in the Human Genome," *Journal of Virology* 71(10):7951-7959, Oct. 1997.

Lacy, Elizabeth, et al., "A Foreign β-Globin Gene in Transgenic Mice: Integration at Abnormal Chromosomal Positions and Expression in Inappropriate Tissues," *Cell* 34:343-358, Sep. 1993.

Rivadeneira, Emilia D., et al., "Sites of recombinant adeno-associated virus integration," *International Journal of Oncology* 12:805-810, 1998.

Fisher-Adams, Grace, et al., "Integration of Adeno-Associated Virus Vectors in CD34+ Human Hematopoietic Progenitor Cells After Transduction," *Blood* 88(2): 492-504, Jul. 15, 1996.

Guis, David R., et al., "Transduced $p16^{INK4a}$ Peptides Inhibit Hypophosphorylation of the Retinoblastoma Protein and Cell Cycle Progession Prior to Activation of Cdk2 Complexes in Late $G_1{}^1$," *Cancer Research* 59:2577-2580, Jun. 1, 1999.

Aints, Alar, et al., "Intercellular Spread of GFP-VP22," *The Journal of Gene Medicine* 1:275-279, 1999.

Chatterjee, Saswati, et al., "Dual-Target Inhibition of HIV-1 in Vitro by Means of an Adeno-Associated Virus Antisense Vector," *Science* 258:1485-1488, Nov. 27, 1992.

Derer, Wolfgang, et al., "Direct protein transfer to terminally differentiated muscle cells," *J. Mol. Med.* 77:609-613, 1999.

* cited by examiner

*Primary Examiner*—Karen Cochrane Carlson
(74) *Attorney, Agent, or Firm*—Rothwell, Figg, Ernst & Manbeck pc

(57) ABSTRACT

This invention pertains to methods for promoting stable and site-specific integration of rep deleted recombinant adeno-associated virus vectors which result in less variable transgene expression and increased safety. These vectors are useful for delivery of a functional gene product to the desired intracellular location.

15 Claims, 11 Drawing Sheets

PKH-LABELED CELLS

VP22 TRANSFECTED

REP490 TRANSFECTED

VP22/PKH MIXTURE

Rep490VP22/PKH MIXTURE

M: 1kb Marker
1: 293 Only
2: Apap + VP22-7gly-Rep491, #2
3: Apap + VP22-7gly-Rep491, #13
4: Apap + VP22-7gly-Rep491, #16
5: Apap + VP22-7gly-Rep491, #33
6: 7374

M: 1kb Marker
1: 293 Only
2: Apap + VP22-7gly-Rep491, #2
3: Apap + VP22-7gly-Rep491, #13
4: Apap + VP22-7gly-Rep491, #16
5: Apap + VP22-7gly-Rep491, #33
6: 7374

```
>gi|341631|gb|M27086.1|HUMAAV02 Homo sapiens DNA fragment containing the 3'
adeno-associated virus/cellular junction Length = 875 Score = 686 bits (346),
Expect = 0.0 Identities = 393/402 (97%), Gaps = 5/402 (1%) Strand = Plus/Plus

Query: 101   tacaggacctccctaa-ccctatgacgtaattcacgtcacgactccttccctgccctgcc  159
              |||||||||||||||| |||||||||||||||||||||||||||||||||||||||||||
Sbjct: 362   tacaggacctccctaatccctatgacgtaattcacgtcacgactccttccctgccctgcc  421
Query: 160   ctctcctgaacctgagccagctcccatagctcagtctggtctatctgcctggccctggcc  219
              ||||||||||||||||||||||||||||||||||||||||||||||||||||||||||| 
Sbjct: 422   ctctcctgaacctgagccagctcccatagctcagtctggtctatctgcctggccctggc-  480
Query: 220   attgtcactttgcgctgccctcctctcgcccccgagtgcccttgctgtgccgccggaact  279
              |||||||||||||||||||||||||||||||| |||||||||||||||||||||||||||
Sbjct: 481   attgtcactttgcgctgccctcctctcgcccc-gagtgcccttgctgtgccgccggaact  539
Query: 280   ctgccctctaacgctgccgtctctcctgagtccggaccactttgagctctactggctt  339
              ||||||||||||||||||||||||||||||||||||||||||||||||||||||||||
Sbjct: 540   ctgccctctaacgctgccgtctctcctgagtccggaccactttgagctctactggctt  599
```

FIG. 11

SEQUENCE LISTING

```
<160> NUMBER OF SEQ ID NOS: 26

<210> SEQ ID NO 1
<211> LENGTH: 33
<212> TYPE: DNA
<213> ORGANISM: Artificial
<220> FEATURE:
<223> OTHER INFORMATION: primer

<400> SEQUENCE: 1

gggaggtttg atatcgcagc cgccatgccg ggg                              33


<210> SEQ ID NO 2
<211> LENGTH: 31
<212> TYPE: DNA
<213> ORGANISM: Artificial
<220> FEATURE:
<223> OTHER INFORMATION: primer

<400> SEQUENCE: 2

gatttaatct agatattgtt caaagatgca g                                31


<210> SEQ ID NO 3
<211> LENGTH: 29
<212> TYPE: DNA
<213> ORGANISM: Artificial
<220> FEATURE:
<223> OTHER INFORMATION: primer

<400> SEQUENCE: 3

ggtttgaacg cgcagatatc atgccgggg                                   29


<210> SEQ ID NO 4
<211> LENGTH: 37
<212> TYPE: DNA
<213> ORGANISM: Artificial
<220> FEATURE:
<223> OTHER INFORMATION: primer

<400> SEQUENCE: 4

gccatacctg atttagcggc cgcattgttc aaagatg                          37
```

-continued

<210> SEQ ID NO 5
<211> LENGTH: 40
<212> TYPE: DNA
<213> ORGANISM: Artificial
<220> FEATURE:
<223> OTHER INFORMATION: primer

<400> SEQUENCE: 5
gattaaaatc atttagcggc cgcagatgca gtcatccaaa 40

<210> SEQ ID NO 6
<211> LENGTH: 36
<212> TYPE: DNA
<213> ORGANISM: Artificial
<220> FEATURE:
<223> OTHER INFORMATION: primer

<400> SEQUENCE: 6
ggctccaccc tttttgtcta gaaattcatg ctccac 36

<210> SEQ ID NO 7
<211> LENGTH: 34
<212> TYPE: DNA
<213> ORGANISM: Artificial
<220> FEATURE:
<223> OTHER INFORMATION: primer

<400> SEQUENCE: 7
gggggcgggt ctttctagag ctccaccctt tttg 34

<210> SEQ ID NO 8
<211> LENGTH: 33
<212> TYPE: DNA
<213> ORGANISM: Artificial
<220> FEATURE:
<223> OTHER INFORMATION: primer

<400> SEQUENCE: 8
gttgatcgaa gcttctagat ctgacgtcga tgg 33

<210> SEQ ID NO 9
<211> LENGTH: 45
<212> TYPE: DNA
<213> ORGANISM: Artificial
<220> FEATURE:
<223> OTHER INFORMATION: primer

<400> SEQUENCE: 9
ccattttgaa gcgatatcgg tggaggcgga gccgccatgc cgggg 45

<210> SEQ ID NO 10
<211> LENGTH: 51
<212> TYPE: DNA
<213> ORGANISM: Artificial
<220> FEATURE:
<223> OTHER INFORMATION: primer

<400> SEQUENCE: 10
gggtctccat ttgatatcgg ggggggtgga ggcggaggcg ccatgccggg g 51

<210> SEQ ID NO 11
<211> LENGTH: 43
<212> TYPE: DNA
<213> ORGANISM: Artificial
<220> FEATURE:
<223> OTHER INFORMATION: primer -continued

<400> SEQUENCE: 11
gatcctttgc ccagcggccg ccagtctttg acttcctgct tgg 43

<210> SEQ ID NO 12
<211> LENGTH: 27
<212> TYPE: DNA
<213> ORGANISM: Artificial
<220> FEATURE:
<223> OTHER INFORMATION: primer

<400> SEQUENCE: 12
ggtcttttgc ggccgccacc ctttttg 27

<210> SEQ ID NO 13
<211> LENGTH: 36
<212> TYPE: DNA
<213> ORGANISM: Artificial
<220> FEATURE:
<223> OTHER INFORMATION: primer

<400> SEQUENCE: 13
gactcgcgca cgcggccgcg ctcacttata tctgcg 36

<210> SEQ ID NO 14
<211> LENGTH: 8
<212> TYPE: PRT
<213> ORGANISM: Artificial
<220> FEATURE:
<223> OTHER INFORMATION: Junction peptide

<400> SEQUENCE: 14

Asp Ile Gln His Ser Gly Gly Arg
1 5

<210> SEQ ID NO 15
<211> LENGTH: 15
<212> TYPE: PRT
<213> ORGANISM: Adeno-associated virus

<400> SEQUENCE: 15

Cys Asp Leu Val Asn Val Asp Leu Asp Asp Cys Ile Phe Glu Gln
1 5 10 15

<210> SEQ ID NO 16
<211> LENGTH: 18
<212> TYPE: PRT
<213> ORGANISM: Artificial
<220> FEATURE:
<223> OTHER INFORMATION: AAVRep 78 variant

<400> SEQUENCE: 16

Cys Asp Leu Val Asn Val Asp Leu Asp Asp Cys Ile Phe Glu Gln Cys
1 5 10 15

Gly Arg

<210> SEQ ID NO 17
<211> LENGTH: 15
<212> TYPE: PRT
<213> ORGANISM: Adeno-associated virus -continued

<400> SEQUENCE: 17

Tyr Val Lys Lys Gly Gly Ala Lys Lys Arg Pro Ala Pro Ser Asp
1 5 10 15

<210> SEQ ID NO 18
<211> LENGTH: 15
<212> TYPE: PRT
<213> ORGANISM: Artificial
<220> FEATURE:
<223> OTHER INFORMATION: AAVRep491 variant

<400> SEQUENCE: 18

Tyr Val Lys Lys Gly Gly Ala Asp Ile Gln His Ser Gly Gly Arg
1 5 10 15

<210> SEQ ID NO 19
<211> LENGTH: 13
<212> TYPE: PRT
<213> ORGANISM: Adeno-associated virus

<400> SEQUENCE: 19

Pro Ala Pro Ser Asp Ala Asp Ile Ser Glu Pro Lys Arg
1 5 10

<210> SEQ ID NO 20
<211> LENGTH: 13
<212> TYPE: PRT
<213> ORGANISM: Artificial
<220> FEATURE:
<223> OTHER INFORMATION: AAVRep505 variant

<400> SEQUENCE: 20

Pro Ala Pro Ser Cys Ala Asp Ile Ser Glu Arg Gly Arg
1 5 10

<210> SEQ ID NO 21
<211> LENGTH: 7871
<212> TYPE: DNA
<213> ORGANISM: Artificial
<220> FEATURE:
<223> OTHER INFORMATION: PVP22 (Gly4) Rep491

<400> SEQUENCE: 21
gacggatcgg gagatctccc gatcccctat ggtcgactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg atgtacgggc cagatatacg cgttgacatt 240
gattattgac tagttattaa tagtaatcaa ttacggggtc attagttcat agcccatata 300
tggagttccg cgttacataa cttacggtaa atggcccgcc tggctgaccg cccaacgacc 360
cccgcccatt gacgtcaata atgacgtatg ttcccatagt aacgccaata gggactttcc 420
attgacgtca atgggtggac tatttacggt aaactgccca cttggcagta catcaagtgt 480
atcatatgcc aagtacgccc cctattgacg tcaatgacgg taaatggccc gcctggcatt 540
atgcccagta catgacctta tgggactttc ctacttggca gtacatctac gtattagtca 600
tcgctattac catggtgatg cggttttggc agtacatcaa tgggcgtgga tagcggtttg 660
actcacgggg atttccaagt ctccacccca ttgacgtcaa tgggagtttg ttttggcacc 720
aaaatcaacg ggactttcca aaatgtcgta acaactccgc cccattgacg caaatgggcg 780
gtaggcgtgt acggtgggag gtctatataa gcagagctct ctggctaact agagaaccca 840

-continued

```
ctgcttactg gcttatcgaa attaatacga ctcactatag ggagacccaa gctggctagt    900

taagcttatt atgacctctc gccgctccgt gaagtcgggt ccgcgggagg ttccgcgcga    960

tgagtacgag gatctgtact acaccccgtc ttcaggtatg gcgagtcccg atagtccgcc   1020

tgacacctcc cgccgtggcg ccctacagac acgctcgcgc cagaggggcg aggtccgttt   1080

cgtccagtac gacgagtcgg attatgccct ctacgggggc tcgtcttccg aagacgacga   1140

acacccggag gtcccccgga cgcggcgtcc cgtttccggg gcggttttgt ccggcccggg   1200

gcctgcgcgg gcgcctccgc cacccgctgg gtccggaggg gccggacgca cacccaccac   1260

cgccccccgg gcccccgaa cccagcgggt ggcgtctaag gcccccgcgg ccccggcggc   1320

ggagaccacc cgcggcagga aatcggccca gccagaatcc gccgcactcc cagacgcccc   1380

cgcgtcgacg gcgccaaccc gatccaagac acccgcgcag gggctggcca gaaagctgca   1440

ctttagcacc gcccccccaa accccgacgc gccatggacc ccccgggtgg ccggctttaa   1500

caagcgcgtc ttctgcgccg cggtcgggcg cctggcggcc atgcatgccc ggatggcggc   1560

tgtccagctc tgggacatgt cgcgtccgcg cacagacgaa gacctcaacg aactccttgg   1620

catcaccacc atccgcgtga cggtctgcga gggcaaaaac ctgcttcagc gcgccaacga   1680

gttggtgaat ccagacgtgg tgcaggacgt cgacgcggcc acggcgactc gagggcgttc   1740

tgcggcgtcg cgccccaccg agcgacctcg agccccagcc cgctccgctt ctcgccccag   1800

acggcccgtc gagggtaccg agctcggatc cactagtcca gtgtggtgga attctgcaga   1860

tatcggtgga ggcggagccg ccatgccggg gttttacgag attgtgatta aggtccccag   1920

cgaccttgac gggcatctgc ccggcatttc tgacagcttt gtgaactggg tggccgagaa   1980

ggaatgggag ttgccgccag attctgacat ggatctgaat ctgattgagc aggcacccct   2040

gaccgtggcc gagaagctgc agcgcgactt tctgacggaa tggcgccgtg tgagtaaggc   2100

cccggaggcc cttttctttg tgcaatttga gaagggagag agctacttcc acatgcacgt   2160

gctcgtggaa accaccgggg tgaaatccat ggttttggga cgtttcctga gtcagattcg   2220

cgaaaaactg attcagagaa tttaccgcgg gatcgagccg actttgccaa actggttcgc   2280

ggtcacaaag accagaaatg gcgccggagg cgggaacaag gtggtggatg agtgctacat   2340

ccccaattac ttgctcccca aaacccagcc tgagctccag tgggcgtgga ctaatatgga   2400

acagtattta agcgcctgtt tgaatctcac ggagcgtaaa cggttggtgg cgcagcatct   2460

gacgcacgtg tcgcagacgc aggagcagaa caaagagaat cagaatccca attctgatgc   2520

gccggtgatc agatcaaaaa cttcagccag gtacatggag ctggtcgggt ggctcgtgga   2580

caaggggatt acctcggaga agcagtggat ccaggaggac caggcctcat acatctcctt   2640

caatgcggcc tccaactcgc ggtcccaaat caaggctgcc ttggacaatg cgggaaagat   2700

tatgagcctg actaaaaccg cccccgacta cctggtgggc cagcagcccg tggaggacat   2760

ttccagcaat cggatttata aaattttgga actaaacggg tacgatcccc aatatgcggc   2820

ttccgtcttt ctgggatggg ccacgaaaaa gttcggcaag aggaacacca tctggctgtt   2880

tgggcctgca actaccggga agaccaacat cgcggaggcc atagcccaca ctgtgccctt   2940

ctacgggtgc gtaaactgga ccaatgagaa ctttcccttc aacgactgtg tcgacaagat   3000

ggtgatctgg tgggaggagg ggaagatgac cgccaaggtc gtggagtcgg ccaaagccat   3060

tctcggagga agcaaggtgc gcgtggacca gaaatgcaag tcctcggccc agatagaccc   3120

gactcccgtg atcgtcacct ccaacaccaa catgtgcgcc gtgattgacg ggaactcaac   3180

gaccttcgaa caccagcagc cgttgcaaga ccggatgttc aaatttgaac tcacccgccg   3240
```

-continued

```
tctggatcat gactttggga aggtcaccaa gcaggaagtc aaagactttt tccggtgggc   3300
aaaggatcac gtggttgagg tggagcatga attctacgtc aaaaagggtg gagctctaga   3360
gggcccgcgg ttcgaacaaa aactcatctc agaagaggat ctgaatatgc ataccggtca   3420
tcatcaccat caccattgag tttaaacccg ctgatcagcc tcgactgtgc cttctagttg   3480
ccagccatct gttgtttgcc cctcccccgt gccttccttg accctggaag gtgccactcc   3540
cactgtcctt tcctaataaa atgaggaaat tgcatcgcat tgtctgagta ggtgtcattc   3600
tattctgggg ggtggggtgg ggcaggacag caagggggag gattgggaag acaatagcag   3660
gcatgctggg gatgcggtgg gctctatggc ttctgaggcg gaaagaacca gctggggctc   3720
tagggggtat ccccacgcgc cctgtagcgg cgcattaagc gcggcgggtg tggtggttac   3780
gcgcagcgtg accgctacac ttgccagcgc cctagcgccc gctcctttcg ctttcttccc   3840
ttcctttctc gccacgttcg ccggctttcc ccgtcaagct ctaaatcggg gcatcccttt   3900
agggttccga tttagtgctt tacggcacct cgaccccaaa aaacttgatt agggtgatgg   3960
ttcacgtagt gggccatcgc cctgatagac ggtttttcgc cctttgacgt tggagtccac   4020
gttctttaat agtggactct tgttccaaac tggaacaaca ctcaacccta tctcggtcta   4080
ttcttttgat ttataaggga ttttggggat ttcggcctat tggttaaaaa atgagctgat   4140
ttaacaaaaa tttaacgcga attaattctg tggaatgtgt gtcagttagg gtgtggaaag   4200
tccccaggct ccccaggcag gcagaagtat gcaaagcatg catctcaatt agtcagcaac   4260
caggtgtgga aagtccccag gctccccagc aggcagaagt atgcaaagca tgcatctcaa   4320
ttagtcagca accatagtcc cgcccctaac tccgcccatc ccgcccctaa ctccgcccag   4380
ttccgcccat tctccgcccc atggctgact aatttttttt atttatgcag aggccgaggc   4440
cgcctctgcc tctgagctat tccagaagta gtgaggaggc ttttttggag gcctaggctt   4500
ttgcaaaaag ctcccgggag cttgtatatc cattttcgga tctgatcaag agacaggatg   4560
aggatcgttt cgcatgattg aacaagatgg attgcacgca ggttctccgg ccgcttgggt   4620
ggagaggcta ttcggctatg actgggcaca acagacaatc ggctgctctg atgccgccgt   4680
gttccggctg tcagcgcagg ggcgcccggt tctttttgtc aagaccgacc tgtccggtgc   4740
cctgaatgaa ctgcaggacg aggcagcgcg gctatcgtgg ctggccacga cgggcgttcc   4800
ttgcgcagct gtgctcgacg ttgtcactga agcgggaagg gactggctgc tattgggcga   4860
agtgccgggg caggatctcc tgtcatctca ccttgctcct gccgagaaag tatccatcat   4920
ggctgatgca atgcggcggc tgcatacgct tgatccggct acctgcccat tcgaccacca   4980
agcgaaacat cgcatcgagc gagcacgtac tcggatggaa gccggtcttg tcgatcagga   5040
tgatctggac gaagagcatc aggggctcgc gccagccgaa ctgttcgcca ggctcaaggc   5100
gcgcatgccc gacggcgagg atctcgtcgt gacccatggc gatgcctgct tgccgaatat   5160
catggtggaa aatggccgct tttctggatt catcgactgt ggccggctgg gtgtggcgga   5220
ccgctatcag gacatagcgt tggctacccg tgatattgct gaagagcttg gcggcgaatg   5280
ggctgaccgc ttcctcgtgc tttacggtat cgccgctccc gattcgcagc gcatcgcctt   5340
ctatcgcctt cttgacgagt tcttctgagc gggactctgg ggttcgcgaa atgaccgacc   5400
aagcgacgcc caacctgcca tcacgagatt tcgattccac cgccgccttc tatgaaaggt   5460
tgggcttcgg aatcgttttc cgggacgccg gctggatgat cctccagcgc ggggatctca   5520
tgctggagtt cttcgcccac cccaacttgt ttattgcagc ttataatggt tacaaataaa   5580
gcaatagcat cacaaatttc acaaataaag catttttttc actgcattct agttgtggtt   5640
```

-continued

```
tgtccaaact catcaatgta tcttatcatg tctgtatacc gtcgacctct agctagagct   5700
tggcgtaatc atggtcatag ctgtttcctg tgtgaaattg ttatccgctc acaattccac   5760
acaacatacg agccggaagc ataaagtgta aagcctgggg tgcctaatga gtgagctaac   5820
tcacattaat tgcgttgcgc tcactgcccg ctttccagtc gggaaacctg tcgtgccagc   5880
tgcattaatg aatcggccaa cgcgcgggga gaggcggttt gcgtattggg cgctcttccg   5940
cttcctcgct cactgactcg ctgcgctcgg tcgttcggct gcggcgagcg gtatcagctc   6000
actcaaaggc ggtaatacgg ttatccacag aatcagggga taacgcagga aagaacatgt   6060
gagcaaaagg ccagcaaaag gccaggaacc gtaaaaaggc cgcgttgctg gcgtttttcc   6120
ataggctccg cccccctgac gagcatcaca aaaatcgacg ctcaagtcag aggtggcgaa   6180
acccgacagg actataaaga taccaggcgt ttccccctgg aagctccctc gtgcgctctc   6240
ctgttccgac cctgccgctt accggatacc tgtccgcctt tctcccttcg ggaagcgtgg   6300
cgctttctca atgctcacgc tgtaggtatc tcagttcggt gtaggtcgtt cgctccaagc   6360
tgggctgtgt gcacgaaccc cccgttcagc ccgaccgctg cgccttatcc ggtaactatc   6420
gtcttgagtc caacccggta agacacgact tatcgccact ggcagcagcc actggtaaca   6480
ggattagcag agcgaggtat gtaggcggtg ctacagagtt cttgaagtgg tggcctaact   6540
acggctacac tagaaggaca gtatttggta tctgcgctct gctgaagcca gttaccttcg   6600
gaaaaagagt tggtagctct tgatccggca aacaaaccac cgctggtagc ggtggttttt   6660
ttgtttgcaa gcagcagatt acgcgcagaa aaaaaggatc tcaagaagat cctttgatct   6720
tttctacggg gtctgacgct cagtggaacg aaaactcacg ttaagggatt ttggtcatga   6780
gattatcaaa aaggatcttc acctagatcc ttttaaatta aaaatgaagt tttaaatcaa   6840
tctaaagtat atatgagtaa acttggtctg acagttacca atgcttaatc agtgaggcac   6900
ctatctcagc gatctgtcta tttcgttcat ccatagttgc ctgactcccc gtcgtgtaga   6960
taactacgat acgggagggc ttaccatctg gccccagtgc tgcaatgata ccgcgagacc   7020
cacgctcacc ggctccagat ttatcagcaa taaaccagcc agccggaagg gccgagcgca   7080
gaagtggtcc tgcaacttta tccgcctcca tccagtctat taattgttgc cgggaagcta   7140
gagtaagtag ttcgccagtt aatagtttgc gcaacgttgt tgccattgct acaggcatcg   7200
tggtgtcacg ctcgtcgttt ggtatggctt cattcagctc cggttcccaa cgatcaaggc   7260
gagttacatg atcccccatg ttgtgcaaaa aagcggttag ctccttcggt cctccgatcg   7320
ttgtcagaag taagttggcc gcagtgttat cactcatggt tatggcagca ctgcataatt   7380
ctcttactgt catgccatcc gtaagatgct tttctgtgac tggtgagtac tcaaccaagt   7440
cattctgaga atagtgtatg cggcgaccga gttgctcttg cccggcgtca atacgggata   7500
ataccgcgcc acatagcaga actttaaaag tgctcatcat tggaaaacgt tcttcggggc   7560
gaaaactctc aaggatctta ccgctgttga gatccagttc gatgtaaccc actcgtgcac   7620
ccaactgatc ttcagcatct tttactttca ccagcgtttc tgggtgagca aaaacaggaa   7680
ggcaaaatgc cgcaaaaaag ggaataaggg cgacacggaa atgttgaata ctcatactct   7740
tcctttttca atattattga agcatttatc agggttattg tctcatgagc ggatacatat   7800
ttgaatgtat ttagaaaaat aaacaaatag gggttccgcg cacatttccc cgaaaagtgc   7860
cacctgacgt c                                                          7871
```

-continued

<210> SEQ ID NO 22
<211> LENGTH: 7828
<212> TYPE: DNA
<213> ORGANISM: Artificial
<220> FEATURE:
<223> OTHER INFORMATION: Rep491VP22

<400> SEQUENCE: 22

```
gacggatcgg gagatctccc gatcccctat ggtcgactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggac tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
actcacgggg atttccaagt ctccacccca ttgacgtcaa tgggagtttg ttttggcacc     720
aaaatcaacg ggactttcca aaatgtcgta acaactccgc cccattgacg caaatgggcg     780
gtaggcgtgt acggtgggag gtctatataa gcagagctct ctggctaact agagaaccca     840
ctgcttactg gcttatcgaa attaatacga ctcactatag ggagacccaa gctggctagt     900
taagcttcca tgccggggtt ttacgagatt gtgattaagg tccccagcga ccttgacggg     960
catctgcccg gcatttctga cagctttgtg aactgggtgg ccgagaagga atgggagttg    1020
ccgccagatt ctgacatgga tctgaatctg attgagcagg cacccctgac cgtggccgag    1080
aagctgcagc gcgactttct gacggaatgg cgccgtgtga gtaaggcccc ggaggccctt    1140
ttctttgtgc aatttgagaa gggagagagc tacttccaca tgcacgtgct cgtggaaacc    1200
accggggtga aatccatggt tttgggacgt ttcctgagtc agattcgcga aaaactgatt    1260
cagagaattt accgcgggat cgagccgact ttgccaaact ggttcgcggt cacaaagacc    1320
agaaatggcg ccggaggcgg gaacaaggtg gtggatgagt gctacatccc caattacttg    1380
ctccccaaaa cccagcctga gctccagtgg gcgtggacta atatggaaca gtatttaagc    1440
gcctgtttga atctcacgga gcgtaaacgg ttggtggcgc agcatctgac gcacgtgtcg    1500
cagacgcagg agcagaacaa agagaatcag aatcccaatt ctgatgcgcc ggtgatcaga    1560
tcaaaaactt cagccaggta catggagctg gtcgggtggc tcgtggacaa ggggattacc    1620
tcggagaagc agtggatcca ggaggaccag gcctcataca tctccttcaa tgcggcctcc    1680
aactcgcggt cccaaatcaa ggctgccttg gacaatgcgg gaaagattat gagcctgact    1740
aaaaccgccc ccgactacct ggtgggccag cagcccgtgg aggacatttc cagcaatcgg    1800
atttataaaa ttttggaact aaacgggtac gatccccaat atgcggcttc cgtctttctg    1860
ggatgggcca cgaaaaagtt cggcaagagg aacaccatct ggctgtttgg gcctgcaact    1920
accgggaaga ccaacatcgc ggaggccata gcccacactg tgcccttcta cgggtgcgta    1980
aactggacca atgagaactt tcccttcaac gactgtgtcg acaagatggt gatctggtgg    2040
gaggagggga agatgaccgc caaggtcgtg gagtcggcca aagccattct cggaggaagc    2100
```

-continued

```
aaggtgcgcg tggaccagaa atgcaagtcc tcggcccaga tagacccgac tcccgtgatc   2160
gtcacctcca acaccaacat gtgcgccgtg attgacggga actcaacgac cttcgaacac   2220
cagcagccgt tgcaagaccg gatgttcaaa tttgaactca cccgccgtct ggatcatgac   2280
tttgggaagg tcaccaagca ggaagtcaaa gactttttcc ggtgggcaaa ggatcacgtg   2340
gttgaggtgg agcatgaatt ctacgtcaaa aagggtggag ccgatatcca gcacagtggc   2400
ggccgcatga cctctcgccg ctccgtgaag tcgggtccgc gggaggttcc gcgcgatgag   2460
tacgaggatc tgtactacac cccgtcttca ggtatggcga gtcccgatag tccgcctgac   2520
acctcccgcc gtggcgccct acagacacgc tcgcgccaga ggggcgaggt ccgtttcgtc   2580
cagtacgacg agtcggatta tgccctctac gggggctcgt cttccgaaga cgacgaacac   2640
ccggaggtcc cccggacgcg gcgtcccgtt tccggggcgg ttttgtccgg cccggggcct   2700
gcgcgggcgc ctccgccacc cgctgggtcc ggaggggccg gacgcacacc caccaccgcc   2760
ccccgggccc cccgaaccca gcgggtggcg tctaaggccc ccgcggcccc ggcggcggag   2820
accacccgcg gcaggaaatc ggcccagcca gaatccgccg cactcccaga cgcccccgcg   2880
tcgacggcgc caacccgatc caagacaccc gcgcaggggc tggccagaaa gctgcacttt   2940
agcaccgccc ccccaaaccc cgacgcgcca tggacccccc gggtggccgg ctttaacaag   3000
cgcgtcttct gcgccgcggt cgggcgcctg gcggccatgc atgcccggat ggcggcggtc   3060
cagctctggg acatgtcgcg tccgcgcaca gacgaagacc tcaacgaact ccttggcatc   3120
accaccatcc gcgtgacggt ctgcgagggc aaaaacctgc ttcagcgcgc caacgagttg   3180
gtgaatccag acgtggtgca ggacgtcgac gcggccacgg cgactcgagg gcgttctgcg   3240
gcgtcgcgcc ccaccgagcg acctcgagcc ccagcccgct ccgcttctcg ccccagacgg   3300
cccgtcgagg gtctagaggg cccgcggttc gaacaaaaac tcatctcaga agaggatctg   3360
aatatgcata ccggtcatca tcaccatcac cattgagttt aaacccgctg atcagcctcg   3420
actgtgcctt ctagttgcca gccatctgtt gtttgcccct cccccgtgcc ttccttgacc   3480
ctggaaggtg ccactcccac tgtcctttcc taataaaatg aggaaattgc atcgcattgt   3540
ctgagtaggt gtcattctat tctggggggt ggggtggggc aggacagcaa gggggaggat   3600
tgggaagaca atagcaggca tgctggggat gcggtgggct ctatggcttc tgaggcggaa   3660
agaaccagct ggggctctag ggggtatccc cacgcgccct gtagcggcgc attaagcgcg   3720
gcgggtgtgg tggttacgcg cagcgtgacc gctacacttg ccagcgccct agcgcccgct   3780
cctttcgctt tcttcccttc ctttctcgcc acgttcgccg gctttccccg tcaagctcta   3840
aatcggggca tccctttagg gttccgattt agtgctttac ggcacctcga ccccaaaaaa   3900
cttgattagg gtgatggttc acgtagtggg ccatcgccct gatagacggt ttttcgccct   3960
ttgacgttgg agtccacgtt ctttaatagt ggactcttgt tccaaactgg aacaacactc   4020
aaccctatct cggtctattc ttttgattta taagggattt tggggatttc ggcctattgg   4080
ttaaaaaatg agctgattta acaaaaattt aacgcgaatt aattctgtgg aatgtgtgtc   4140
agttagggtg tggaaagtcc ccaggctccc caggcaggca gaagtatgca aagcatgcat   4200
ctcaattagt cagcaaccag gtgtggaaag tccccaggct ccccagcagg cagaagtatg   4260
caaagcatgc atctcaatta gtcagcaacc atagtcccgc ccctaactcc gcccatcccg   4320
cccctaactc cgcccagttc cgcccattct ccgccccatg gctgactaat tttttttatt   4380
tatgcagagg ccgaggccgc ctctgcctct gagctattcc agaagtagtg aggaggcttt   4440
tttggaggcc taggcttttg caaaaagctc ccgggagctt gtatatccat tttcggatct   4500
```

-continued

```
gatcaagaga caggatgagg atcgtttcgc atgattgaac aagatggatt gcacgcaggt   4560
tctccggccg cttgggtgga gaggctattc ggctatgact gggcacaaca gacaatcggc   4620
tgctctgatg ccgccgtgtt ccggctgtca gcgcaggggc gcccggttct ttttgtcaag   4680
accgacctgt ccggtgccct gaatgaactg caggacgagg cagcgcggct atcgtggctg   4740
gccacgacgg gcgttccttg cgcagctgtg ctcgacgttg tcactgaagc gggaagggac   4800
tggctgctat tgggcgaagt gccggggcag gatctcctgt catctcacct tgctcctgcc   4860
gagaaagtat ccatcatggc tgatgcaatg cggcggctgc atacgcttga tccggctacc   4920
tgcccattcg accaccaagc gaaacatcgc atcgagcgag cacgtactcg gatggaagcc   4980
ggtcttgtcg atcaggatga tctggacgaa gagcatcagg ggctcgcgcc agccgaactg   5040
ttcgccaggc tcaaggcgcg catgcccgac ggcgaggatc tcgtcgtgac ccatggcgat   5100
gcctgcttgc cgaatatcat ggtggaaaat ggccgctttt ctggattcat cgactgtggc   5160
cggctgggtg tggcggaccg ctatcaggac atagcgttgg ctacccgtga tattgctgaa   5220
gagcttggcg gcgaatgggc tgaccgcttc ctcgtgcttt acggtatcgc cgctcccgat   5280
tcgcagcgca tcgccttcta tcgccttctt gacgagttct tctgagcggg actctggggt   5340
tcgcgaaatg accgaccaag cgacgcccaa cctgccatca cgagatttcg attccaccgc   5400
cgccttctat gaaaggttgg gcttcggaat cgttttccgg gacgccggct ggatgatcct   5460
ccagcgcggg gatctcatgc tggagttctt cgcccacccc aacttgttta ttgcagctta   5520
taatggttac aaataaagca atagcatcac aaatttcaca aataaagcat ttttttcact   5580
gcattctagt tgtggtttgt ccaaactcat caatgtatct tatcatgtct gtataccgtc   5640
gacctctagc tagagcttgg cgtaatcatg gtcatagctg tttcctgtgt gaaattgtta   5700
tccgctcaca attccacaca acatacgagc cggaagcata aagtgtaaag cctggggtgc   5760
ctaatgagtg agctaactca cattaattgc gttgcgctca ctgcccgctt tccagtcggg   5820
aaacctgtcg tgccagctgc attaatgaat cggccaacgc gcggggagag gcggtttgcg   5880
tattgggcgc tcttccgctt cctcgctcac tgactcgctg cgctcggtcg ttcggctgcg   5940
gcgagcggta tcagctcact caaaggcggt aatacggtta tccacagaat caggggataa   6000
cgcaggaaag aacatgtgag caaaaggcca gcaaaaggcc aggaaccgta aaaaggccgc   6060
gttgctggcg tttttccata ggctccgccc ccctgacgag catcacaaaa atcgacgctc   6120
aagtcagagg tggcgaaacc cgacaggact ataaagatac caggcgtttc cccctggaag   6180
ctccctcgtg cgctctcctg ttccgaccct gccgcttacc ggatacctgt ccgcctttct   6240
cccttcggga agcgtggcgc tttctcaatg ctcacgctgt aggtatctca gttcggtgta   6300
ggtcgttcgc tccaagctgg gctgtgtgca cgaacccccc gttcagcccg accgctgcgc   6360
cttatccggt aactatcgtc ttgagtccaa cccggtaaga cacgacttat cgccactggc   6420
agcagccact ggtaacagga ttagcagagc gaggtatgta ggcggtgcta cagagttctt   6480
gaagtggtgg cctaactacg gctacactag aaggacagta tttggtatct gcgctctgct   6540
gaagccagtt accttcggaa aaagagttgg tagctcttga tccggcaaac aaaccaccgc   6600
tggtagcggt ggtttttttg tttgcaagca gcagattacg cgcagaaaaa aaggatctca   6660
agaagatcct ttgatctttt ctacggggtc tgacgctcag tggaacgaaa actcacgtta   6720
agggattttg gtcatgagat tatcaaaaag gatcttcacc tagatccttt taaattaaaa   6780
atgaagtttt aaatcaatct aaagtatata tgagtaaact tggtctgaca gttaccaatg   6840
cttaatcagt gaggcaccta tctcagcgat ctgtctattt cgttcatcca tagttgcctg   6900
```

-continued

```
actccccgtc gtgtagataa ctacgatacg ggagggctta ccatctggcc ccagtgctgc   6960

aatgataccg cgagacccac gctcaccggc tccagattta tcagcaataa accagccagc   7020

cggaagggcc gagcgcagaa gtggtcctgc aactttatcc gcctccatcc agtctattaa   7080

ttgttgccgg gaagctagag taagtagttc gccagttaat agtttgcgca acgttgttgc   7140

cattgctaca ggcatcgtgg tgtcacgctc gtcgtttggt atggcttcat tcagctccgg   7200

ttcccaacga tcaaggcgag ttacatgatc ccccatgttg tgcaaaaaag cggttagctc   7260

cttcggtcct ccgatcgttg tcagaagtaa gttggccgca gtgttatcac tcatggttat   7320

ggcagcactg cataattctc ttactgtcat gccatccgta agatgctttt ctgtgactgg   7380

tgagtactca accaagtcat tctgagaata gtgtatgcgg cgaccgagtt gctcttgccc   7440

ggcgtcaata cgggataata ccgcgccaca tagcagaact ttaaaagtgc tcatcattgg   7500

aaaacgttct tcggggcgaa aactctcaag gatcttaccg ctgttgagat ccagttcgat   7560

gtaacccact cgtgcaccca actgatcttc agcatctttt actttcacca gcgtttctgg   7620

gtgagcaaaa acaggaaggc aaaatgccgc aaaaaaggga ataagggcga cacggaaatg   7680

ttgaatactc atactcttcc tttttcaata ttattgaagc atttatcagg gttattgtct   7740

catgagcgga tacatatttg aatgtattta gaaaaataaa caaatagggg ttccgcgcac   7800

atttccccga aaagtgccac ctgacgtc                                       7828
```

<210> SEQ ID NO 23
<211> LENGTH: 7856
<212> TYPE: DNA
<213> ORGANISM: Artificial
<220> FEATURE:
<223> OTHER INFORMATION: RepVP22-R490

<400> SEQUENCE: 23

```
gacggatcgg gagatctccc gatcccctat ggtcgactct cagtacaatc tgctctgatg     60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180

ttagggttag gcgttttgcg ctgcttcgcg atgtacgggc cagatatacg cgttgacatt    240

gattattgac tagttattaa tagtaatcaa ttacggggtc attagttcat agcccatata    300

tggagttccg cgttacataa cttacggtaa atggcccgcc tggctgaccg cccaacgacc    360

cccgcccatt gacgtcaata atgacgtatg ttcccatagt aacgccaata gggactttcc    420

attgacgtca atgggtggac tatttacggt aaactgccca cttggcagta catcaagtgt    480

atcatatgcc aagtacgccc cctattgacg tcaatgacgg taaatggccc gcctggcatt    540

atgcccagta catgacctta tgggactttc ctacttggca gtacatctac gtattagtca    600

tcgctattac catggtgatg cggttttggc agtacatcaa tgggcgtgga tagcggtttg    660

actcacgggg atttccaagt ctccacccca ttgacgtcaa tgggagtttg ttttggcacc    720

aaaatcaacg ggactttcca aaatgtcgta acaactccgc cccattgacg caaatgggcg    780

gtaggcgtgt acggtgggag gtctatataa gcagagctct ctggctaact agagaaccca    840

ctgcttactg gcttatcgaa attaatacga ctcactatag ggagacccaa gctggctagt    900

taagcttggt accgagctcg gatccactag tccagtgtgg tggaattctg cagatatcat    960

gccggggttt tacgagattg tgattaaggt ccccagcgac cttgacgggc atctgcccgg   1020

catttctgac agctttgtga actgggtggc cgagaaggaa tgggagttgc cgccagattc   1080

tgacatggat ctgaatctga ttgagcaggc acccctgacc gtggccgaga agctgcagcg   1140
```

-continued

```
cgactttctg acggaatggc gccgtgtgag taaggccccg gaggcccttt tctttgtgca   1200
atttgagaag ggagagagct acttccacat gcacgtgctc gtggaaacca ccggggtgaa   1260
atccatggtt ttgggacgtt tcctgagtca gattcgcgaa aaactgattc agagaattta   1320
ccgcgggatc gagccgactt tgccaaactg gttcgcggtc acaaagacca gaaatggcgc   1380
cggaggcggg aacaaggtgg tggatgagtg ctacatcccc aattacttgc tccccaaaac   1440
ccagcctgag ctccagtggg cgtggactaa tatggaacag tatttaagcg cctgtttgaa   1500
tctcacggag cgtaaacggt tggtggcgca gcatctgacg cacgtgtcgc agacgcagga   1560
gcagaacaaa gagaatcaga atcccaattc tgatgcgccg gtgatcagat caaaaacttc   1620
agccaggtac atggagctgg tcgggtggct cgtggacaag gggattacct cggagaagca   1680
gtggatccag gaggaccagg cctcatacat ctccttcaat gcggcctcca actcgcggtc   1740
ccaaatcaag gctgccttgg acaatgcggg aaagattatg agcctgacta aaaccgcccc   1800
cgactacctg gtgggccagc agcccgtgga ggacatttcc agcaatcgga tttataaaat   1860
tttggaacta aacgggtacg atccccaata tgcggcttcc gtctttctgg gatgggccac   1920
gaaaaagttc ggcaagagga acaccatctg gctgtttggg cctgcaacta ccgggaagac   1980
caacatcgcg gaggccatag cccacactgt gcccttctac gggtgcgtaa actggaccaa   2040
tgagaacttt cccttcaacg actgtgtcga caagatggtg atctggtggg aggaggggaa   2100
gatgaccgcc aaggtcgtgg agtcggccaa agccattctc ggaggaagca aggtgcgcgt   2160
ggaccagaaa tgcaagtcct cggcccagat agacccgact cccgtgatcg tcacctccaa   2220
caccaacatg tgcgccgtga ttgacgggaa ctcaacgacc ttcgaacacc agcagccgtt   2280
gcaagaccgg atgttcaaat ttgaactcac ccgccgtctg gatcatgact ttgggaaggt   2340
caccaagcag gaagtcaaag actttttccg gtgggcaaag gatcacgtgg ttgaggtgga   2400
gcatgaattc tacgtcaaaa agggtggcgg ccgcatgacc tctcgccgct ccgtgaagtc   2460
gggtccgcgg gaggttccgc gcgatgagta cgaggatctg tactacaccc cgtcttcagg   2520
tatggcgagt cccgatagtc cgcctgacac ctcccgccgt ggcgccctac agacacgctc   2580
gcgccagagg ggcgaggtcc gtttcgtcca gtacgacgag tcggattatg ccctctacgg   2640
gggctcgtct tccgaagacg acgaacaccc ggaggtcccc cggacgcggc gtcccgtttc   2700
cggggcggtt ttgtccggcc cggggcctgc gcgggcgcct ccgccacccg ctgggtccgg   2760
aggggccgga cgcacaccca ccaccgcccc ccgggccccc cgaacccagc gggtggcgtc   2820
taaggccccc gcggccccgg cggcggagac cacccgcggc aggaaatcgg cccagccaga   2880
atccgccgca ctcccagacg cccccgcgtc gacggcgcca acccgatcca agacacccgc   2940
gcaggggctg gccagaaagc tgcactttag caccgccccc ccaaaccccg acgcgccatg   3000
gacccccggg gtggccggct ttaacaagcg cgtcttctgc gccgcggtcg ggcgcctggc   3060
ggccatgcat gcccggatgg cggcggtcca gctctgggac atgtcgcgtc cgcgcacaga   3120
cgaagacctc aacgaactcc ttggcatcac caccatccgc gtgacggtct gcgagggcaa   3180
aaacctgctt cagcgcgcca acgagttggt gaatccagac gtggtgcagg acgtcgacgc   3240
ggccacggcg actcgagggc gttctgcggc gtcgcgcccc accgagcgac ctcgagcccc   3300
agcccgctcc gcttctcgcc ccagacggcc cgtcgagggt ctagagggcc cgcggttcga   3360
acaaaaactc atctcagaag aggatctgaa tatgcatacc ggtcatcatc accatcacca   3420
ttgagtttaa acccgctgat cagcctcgac tgtgccttct agttgccagc catctgttgt   3480
ttgcccctcc cccgtgcctt ccttgaccct ggaaggtgcc actcccactg tcctttccta   3540
```

-continued

```
ataaaatgag gaaattgcat cgcattgtct gagtaggtgt cattctattc tggggggtgg   3600
ggtggggcag gacagcaagg gggaggattg ggaagacaat agcaggcatg ctggggatgc   3660
ggtgggctct atggcttctg aggcggaaag aaccagctgg ggctctaggg ggtatcccca   3720
cgcgccctgt agcggcgcat taagcgcggc gggtgtggtg gttacgcgca gcgtgaccgc   3780
tacacttgcc agcgccctag cgcccgctcc tttcgctttc ttcccttcct ttctcgccac   3840
gttcgccggc tttccccgtc aagctctaaa tcggggcatc cctttagggt tccgatttag   3900
tgctttacgg cacctcgacc ccaaaaaact tgattagggt gatggttcac gtagtgggcc   3960
atcgccctga tagacggttt ttcgcccttt gacgttggag tccacgttct ttaatagtgg   4020
actcttgttc caaactggaa caacactcaa ccctatctcg gtctattctt ttgatttata   4080
agggattttg gggatttcgg cctattggtt aaaaaatgag ctgatttaac aaaaatttaa   4140
cgcgaattaa ttctgtggaa tgtgtgtcag ttagggtgtg gaaagtcccc aggctcccca   4200
ggcaggcaga agtatgcaaa gcatgcatct caattagtca gcaaccaggt gtggaaagtc   4260
cccaggctcc ccagcaggca gaagtatgca aagcatgcat ctcaattagt cagcaaccat   4320
agtcccgccc ctaactccgc ccatcccgcc cctaactccg cccagttccg cccattctcc   4380
gccccatggc tgactaattt tttttattta tgcagaggcc gaggccgcct ctgcctctga   4440
gctattccag aagtagtgag gaggcttttt tggaggccta ggcttttgca aaaagctccc   4500
gggagcttgt atatccattt tcggatctga tcaagagaca ggatgaggat cgtttcgcat   4560
gattgaacaa gatggattgc acgcaggttc tccggccgct tgggtggaga ggctattcgg   4620
ctatgactgg gcacaacaga caatcggctg ctctgatgcc gccgtgttcc ggctgtcagc   4680
gcaggggcgc ccggttcttt ttgtcaagac cgacctgtcc ggtgccctga atgaactgca   4740
ggacgaggca gcgcggctat cgtggctggc cacgacgggc gttccttgcg cagctgtgct   4800
cgacgttgtc actgaagcgg gaagggactg gctgctattg ggcgaagtgc cggggcagga   4860
tctcctgtca tctcaccttg ctcctgccga gaaagtatcc atcatggctg atgcaatgcg   4920
gcggctgcat acgcttgatc cggctacctg cccattcgac caccaagcga aacatcgcat   4980
cgagcgagca cgtactcgga tggaagccgg tcttgtcgat caggatgatc tggacgaaga   5040
gcatcagggg ctcgcgccag ccgaactgtt cgccaggctc aaggcgcgca tgcccgacgg   5100
cgaggatctc gtcgtgaccc atggcgatgc ctgcttgccg aatatcatgg tggaaaatgg   5160
ccgcttttct ggattcatcg actgtggccg gctgggtgtg gcggaccgct atcaggacat   5220
agcgttggct acccgtgata ttgctgaaga gcttggcggc gaatgggctg accgcttcct   5280
cgtgctttac ggtatcgccg ctcccgattc gcagcgcatc gccttctatc gccttcttga   5340
cgagttcttc tgagcgggac tctggggttc gcgaaatgac cgaccaagcg acgcccaacc   5400
tgccatcacg agatttcgat tccaccgccg ccttctatga aaggttgggc ttcggaatcg   5460
ttttccggga cgccggctgg atgatcctcc agcgcgggga tctcatgctg gagttcttcg   5520
cccaccccaa cttgtttatt gcagcttata atggttacaa ataaagcaat agcatcacaa   5580
atttcacaaa taaagcattt ttttcactgc attctagttg tggtttgtcc aaactcatca   5640
atgtatctta tcatgtctgt ataccgtcga cctctagcta gagcttggcg taatcatggt   5700
catagctgtt tcctgtgtga aattgttatc cgctcacaat tccacacaac atacgagccg   5760
gaagcataaa gtgtaaagcc tggggtgcct aatgagtgag ctaactcaca ttaattgcgt   5820
tgcgctcact gcccgctttc cagtcgggaa acctgtcgtg ccagctgcat taatgaatcg   5880
gccaacgcgc ggggagaggc ggtttgcgta ttgggcgctc ttccgcttcc tcgctcactg   5940
```

-continued

```
actcgctgcg ctcggtcgtt cggctgcggc gagcggtatc agctcactca aaggcggtaa   6000

tacggttatc cacagaatca ggggataacg caggaaagaa catgtgagca aaaggccagc   6060

aaaaggccag gaaccgtaaa aaggccgcgt tgctggcgtt tttccatagg ctccgccccc   6120

ctgacgagca tcacaaaaat cgacgctcaa gtcagaggtg gcgaaacccg acaggactat   6180

aaagatacca ggcgtttccc cctggaagct ccctcgtgcg ctctcctgtt ccgaccctgc   6240

cgcttaccgg atacctgtcc gcctttctcc cttcgggaag cgtggcgctt tctcaatgct   6300

cacgctgtag gtatctcagt tcggtgtagg tcgttcgctc caagctgggc tgtgtgcacg   6360

aaccccccgt tcagcccgac cgctgcgcct tatccggtaa ctatcgtctt gagtccaacc   6420

cggtaagaca cgacttatcg ccactggcag cagccactgg taacaggatt agcagagcga   6480

ggtatgtagg cggtgctaca gagttcttga agtggtggcc taactacggc tacactagaa   6540

ggacagtatt tggtatctgc gctctgctga agccagttac cttcggaaaa agagttggta   6600

gctcttgatc cggcaaacaa accaccgctg gtagcggtgg tttttttgtt tgcaagcagc   6660

agattacgcg cagaaaaaaa ggatctcaag aagatccttt gatcttttct acggggtctg   6720

acgctcagtg gaacgaaaac tcacgttaag ggattttggt catgagatta tcaaaaagga   6780

tcttcaccta gatcctttta aattaaaaat gaagttttaa atcaatctaa agtatatatg   6840

agtaaacttg gtctgacagt taccaatgct taatcagtga ggcacctatc tcagcgatct   6900

gtctatttcg ttcatccata gttgcctgac tccccgtcgt gtagataact acgatacggg   6960

agggcttacc atctggcccc agtgctgcaa tgataccgcg agacccacgc tcaccggctc   7020

cagatttatc agcaataaac cagccagccg gaagggccga gcgcagaagt ggtcctgcaa   7080

ctttatccgc ctccatccag tctattaatt gttgccggga agctagagta agtagttcgc   7140

cagttaatag tttgcgcaac gttgttgcca ttgctacagg catcgtggtg tcacgctcgt   7200

cgtttggtat ggcttcattc agctccggtt cccaacgatc aaggcgagtt acatgatccc   7260

ccatgttgtg caaaaaagcg gttagctcct tcggtcctcc gatcgttgtc agaagtaagt   7320

tggccgcagt gttatcactc atggttatgg cagcactgca taattctctt actgtcatgc   7380

catccgtaag atgcttttct gtgactggtg agtactcaac caagtcattc tgagaatagt   7440

gtatgcggcg accgagttgc tcttgcccgg cgtcaatacg ggataatacc gcgccacata   7500

gcagaacttt aaaagtgctc atcattggaa aacgttcttc ggggcgaaaa ctctcaagga   7560

tcttaccgct gttgagatcc agttcgatgt aacccactcg tgcacccaac tgatcttcag   7620

catcttttac tttcaccagc gtttctgggt gagcaaaaac aggaaggcaa aatgccgcaa   7680

aaaagggaat aagggcgaca cggaaatgtt gaatactcat actcttcctt tttcaatatt   7740

attgaagcat ttatcagggt tattgtctca tgagcggata catatttgaa tgtatttaga   7800

aaaataaaca aataggggtt ccgcgcacat ttccccgaaa agtgccacct gacgtc       7856
```

<210> SEQ ID NO 24
<211> LENGTH: 8252
<212> TYPE: DNA
<213> ORGANISM: Artificial
<220> FEATURE:
<223> OTHER INFORMATION: VP22#2-RepVP5-EcRV-S-Cys

<400> SEQUENCE: 24

```
gacggatcgg gagatctccc gatcccctat ggtcgactct cagtacaatc tgctctgatg     60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180
```

-continued

```
ttagggttag gcgttttgcg ctgcttcgcg atgtacgggc cagatatacg cgttgacatt    240

gattattgac tagttattaa tagtaatcaa ttacggggtc attagttcat agcccatata    300

tggagttccg cgttacataa cttacggtaa atggcccgcc tggctgaccg cccaacgacc    360

cccgcccatt gacgtcaata atgacgtatg ttcccatagt aacgccaata gggactttcc    420

attgacgtca atgggtggac tatttacggt aaactgccca cttggcagta catcaagtgt    480

atcatatgcc aagtacgccc cctattgacg tcaatgacgg taaatggccc gcctggcatt    540

atgcccagta catgacctta tgggactttc ctacttggca gtacatctac gtattagtca    600

tcgctattac catggtgatg cggttttggc agtacatcaa tgggcgtgga tagcggtttg    660

actcacgggg atttccaagt ctccacccca ttgacgtcaa tgggagtttg ttttggcacc    720

aaaatcaacg ggactttcca aaatgtcgta acaactccgc cccattgacg caaatgggcg    780

gtaggcgtgt acggtgggag gtctatataa gcagagctct ctggctaact agagaaccca    840

ctgcttactg gcttatcgaa attaatacga ctcactatag ggagacccaa gctggctagt    900

taagcttggt accgagctcg gatccactag tccagtgtgg tggaattctg cagatatcat    960

gccggggttt tacgagattg tgattaaggt ccccagcgac cttgacgggc atctgcccgg   1020

catttctgac agctttgtga actgggtggc cgagaaggaa tgggagttgc cgccagattc   1080

tgacatggat ctgaatctga ttgagcaggc acccctgacc gtggccgaga agctgcagcg   1140

cgactttctg acggaatggc gccgtgtgag taaggccccg gaggcccttt tctttgtgca   1200

atttgagaag ggagagagct acttccacat gcacgtgctc gtggaaacca ccggggtgaa   1260

atccatggtt ttgggacgtt tcctgagtca gattcgcgaa aaactgattc agagaattta   1320

ccgcgggatc gagccgactt tgccaaactg gttcgcggtc acaaagacca gaaatggcgc   1380

cggaggcggg aacaaggtgg tggatgagtg ctacatcccc aattacttgc tccccaaaac   1440

ccagcctgag ctccagtggg cgtggactaa tatggaacag tatttaagcg cctgtttgaa   1500

tctcacggag cgtaaacggt tggtggcgca gcatctgacg cacgtgtcgc agacgcagga   1560

gcagaacaaa gagaatcaga atcccaattc tgatgcgccg gtgatcagat caaaaacttc   1620

agccaggtac atggagctgg tcgggtggct cgtggacaag gggattacct cggagaagca   1680

gtggatccag gaggaccagg cctcatacat ctccttcaat gcggcctcca actcgcggtc   1740

ccaaatcaag gctgccttgg acaatgcggg aaagattatg agcctgacta aaaccgcccc   1800

cgactacctg gtgggccagc agcccgtgga ggacatttcc agcaatcgga tttataaaat   1860

tttggaacta aacgggtacg atccccaata tgcggcttcc gtctttctgg gatgggccac   1920

gaaaaagttc ggcaagagga acaccatctg gctgtttggg cctgcaacta ccgggaagac   1980

caacatcgcg gaggccatag cccacactgt gcccttctac gggtgcgtaa actggaccaa   2040

tgagaacttt cccttcaacg actgtgtcga caagatggtg atctggtggg aggaggggaa   2100

gatgaccgcc aaggtcgtgg agtcggccaa agccattctc ggaggaagca aggtgcgcgt   2160

ggaccagaaa tgcaagtcct cggcccagat agacccgact cccgtgatcg tcacctccaa   2220

caccaacatg tgcgccgtga ttgacgggaa ctcaacgacc ttcgaacacc agcagccgtt   2280

gcaagaccgg atgttcaaat ttgaactcac ccgccgtctg gatcatgact ttgggaaggt   2340

caccaagcag gaagtcaaag actttttccg gtgggcaaag gatcacgtgg ttgaggtgga   2400

gcatgaattc tacgtcaaaa agggtggagc caagaaaaga cccgccccca gtgacgcaga   2460

tataagtgag cccaaacggg tgcgcgagtc agttgcgcag ccatcgacgt cagacgcgga   2520

agcttcgatc aactacgcag acaggtacca aaacaaatgt tctcgtcacg tgggcatgaa   2580
```

-continued

```
tctgatgctg tttccctgca gacaatgcga gagaatgaat cagaattcaa atatctgctt   2640
cactcacgga cagaaagact gtttagagtg ctttcccgtg tcagaatctc aacccgtttc   2700
tgtcgtcaaa aaggcgtatc agaaactgtg ctacattcat catatcatgg gaaaggtgcc   2760
agacgcttgc actgcctgcg atctggtcaa tgtggatttg gatgactgca tctttgaaca   2820
atgcggccgc atgacctctc gccgctccgt gaagtcgggt ccgcgggagg ttccgcgcga   2880
tgagtacgag gatctgtact acaccccgtc ttcaggtatg gcgagtcccg atagtccgcc   2940
tgacacctcc cgccgtggcg ccctacagac acgctcgcgc cagaggggcg aggtccgttt   3000
cgtccagtac gacgagtcgg attatgccct ctacgggggc tcgtcttccg aagacgacga   3060
acacccggag gtcccccgga cgcggcgtcc cgtttccggg gcggttttgt ccggcccggg   3120
gcctgcgcgg gcgcctccgc cacccgctgg gtccggaggg gccggacgca cacccaccac   3180
cgcccccggg gccccccgaa cccagcgggt ggcgtctaag gcccccgcgg ccccggcggc   3240
ggagaccacc cgcggcagga aatcggccca gccagaatcc gccgcactcc cagacgcccc   3300
cgcgtcgacg gcgccaaccc gatccaagac acccgcgcag gggctggcca gaaagctgca   3360
ctttagcacc gccccccaa accccgacgc gccatggacc ccccgggtgg ccggctttaa   3420
caagcgcgtc ttctgcgccg cggtcgggcg cctggcggcc atgcatgccc ggatggcggc   3480
ggtccagctc tgggacatgt cgcgtccgcg cacagacgaa gacctcaacg aactccttgg   3540
catcaccacc atccgcgtga cggtctgcga gggcaaaaac ctgcttcagc gcgccaacga   3600
gttggtgaat ccagacgtgg tgcaggacgt cgacgcggcc acggcgactc gagggcgttc   3660
tgcggcgtcg cgccccaccg agcgacctcg agccccagcc cgctccgctt ctcgccccag   3720
acggcccgtc gagggtctag agggcccgcg gttcgaacaa aaactcatct cagaagagga   3780
tctgaatatg cataccggtc atcatcacca tcaccattga gtttaaaccc gctgatcagc   3840
ctcgactgtg ccttctagtt gccagccatc tgttgtttgc ccctcccccg tgccttcctt   3900
gaccctggaa ggtgccactc ccactgtcct ttcctaataa aatgaggaaa ttgcatcgca   3960
ttgtctgagt aggtgtcatt ctattctggg gggtggggtg gggcaggaca gcaaggggga   4020
ggattgggaa gacaatagca ggcatgctgg ggatgcggtg ggctctatgg cttctgaggc   4080
ggaaagaacc agctggggct ctagggggta tccccacgcg ccctgtagcg gcgcattaag   4140
cgcggcgggt gtggtggtta cgcgcagcgt gaccgctaca cttgccagcg ccctagcgcc   4200
cgctcctttc gctttcttcc cttcctttct cgccacgttc gccggctttc cccgtcaagc   4260
tctaaatcgg ggcatccctt tagggttccg atttagtgct ttacggcacc tcgaccccaa   4320
aaaacttgat tagggtgatg gttcacgtag tgggccatcg ccctgataga cggtttttcg   4380
ccctttgacg ttggagtcca cgttctttaa tagtggactc ttgttccaaa ctggaacaac   4440
actcaaccct atctcggtct attcttttga tttataaggg attttgggga tttcggccta   4500
ttggttaaaa aatgagctga tttaacaaaa atttaacgcg aattaattct gtggaatgtg   4560
tgtcagttag ggtgtggaaa gtccccaggc tccccaggca ggcagaagta tgcaaagcat   4620
gcatctcaat tagtcagcaa ccaggtgtgg aaagtcccca ggctccccag caggcagaag   4680
tatgcaaagc atgcatctca attagtcagc aaccatagtc ccgcccctaa ctccgcccat   4740
cccgccccta actccgccca gttccgccca ttctccgccc catggctgac taattttttt   4800
tatttatgca gaggccgagg ccgcctctgc ctctgagcta ttccagaagt agtgaggagg   4860
ctttttttgga ggcctaggct tttgcaaaaa gctcccggga gcttgtatat ccattttcgg   4920
atctgatcaa gagacaggat gaggatcgtt tcgcatgatt gaacaagatg gattgcacgc   4980
```

-continued

```
aggttctccg gccgcttggg tggagaggct attcggctat gactgggcac aacagacaat   5040
cggctgctct gatgccgccg tgttccggct gtcagcgcag gggcgcccgg ttctttttgt   5100
caagaccgac ctgtccggtg ccctgaatga actgcaggac gaggcagcgc ggctatcgtg   5160
gctggccacg acgggcgttc cttgcgcagc tgtgctcgac gttgtcactg aagcgggaag   5220
ggactggctg ctattgggcg aagtgccggg gcaggatctc ctgtcatctc accttgctcc   5280
tgccgagaaa gtatccatca tggctgatgc aatgcggcgg ctgcatacgc ttgatccggc   5340
tacctgccca ttcgaccacc aagcgaaaca tcgcatcgag cgagcacgta ctcggatgga   5400
agccggtctt gtcgatcagg atgatctgga cgaagagcat caggggctcg cgccagccga   5460
actgttcgcc aggctcaagg cgcgcatgcc cgacggcgag gatctcgtcg tgacccatgg   5520
cgatgcctgc ttgccgaata tcatggtgga aaatggccgc ttttctggat tcatcgactg   5580
tggccggctg ggtgtggcgg accgctatca ggacatagcg ttggctaccc gtgatattgc   5640
tgaagagctt ggcggcgaat gggctgaccg cttcctcgtg ctttacggta tcgccgctcc   5700
cgattcgcag cgcatcgcct tctatcgcct tcttgacgag ttcttctgag cgggactctg   5760
gggttcgcga aatgaccgac caagcgacgc ccaacctgcc atcacgagat ttcgattcca   5820
ccgccgcctt ctatgaaagg ttgggcttcg gaatcgtttt ccgggacgcc ggctggatga   5880
tcctccagcg cggggatctc atgctggagt tcttcgccca ccccaacttg tttattgcag   5940
cttataatgg ttacaaataa agcaatagca tcacaaattt cacaaataaa gcattttttt   6000
cactgcattc tagttgtggt ttgtccaaac tcatcaatgt atcttatcat gtctgtatac   6060
cgtcgacctc tagctagagc ttggcgtaat catggtcata gctgtttcct gtgtgaaatt   6120
gttatccgct cacaattcca cacaacatac gagccggaag cataaagtgt aaagcctggg   6180
gtgcctaatg agtgagctaa ctcacattaa ttgcgttgcg ctcactgccc gctttccagt   6240
cgggaaacct gtcgtgccag ctgcattaat gaatcggcca acgcgcgggg agaggcggtt   6300
tgcgtattgg gcgctcttcc gcttcctcgc tcactgactc gctgcgctcg gtcgttcggc   6360
tgcggcgagc ggtatcagct cactcaaagg cggtaatacg gttatccaca gaatcagggg   6420
ataacgcagg aaagaacatg tgagcaaaag gccagcaaaa ggccaggaac cgtaaaaagg   6480
ccgcgttgct ggcgtttttc cataggctcc gcccccctga cgagcatcac aaaaatcgac   6540
gctcaagtca gaggtggcga aacccgacag gactataaag ataccaggcg tttccccctg   6600
gaagctccct cgtgcgctct cctgttccga ccctgccgct taccggatac ctgtccgcct   6660
ttctcccttc gggaagcgtg gcgctttctc aatgctcacg ctgtaggtat ctcagttcgg   6720
tgtaggtcgt tcgctccaag ctgggctgtg tgcacgaacc ccccgttcag cccgaccgct   6780
gcgccttatc cggtaactat cgtcttgagt ccaacccggt aagacacgac ttatcgccac   6840
tggcagcagc cactggtaac aggattagca gagcgaggta tgtaggcggt gctacagagt   6900
tcttgaagtg gtggcctaac tacggctaca ctagaaggac agtatttggt atctgcgctc   6960
tgctgaagcc agttaccttc ggaaaaagag ttggtagctc ttgatccggc aaacaaacca   7020
ccgctggtag cggtggtttt tttgtttgca agcagcagat tacgcgcaga aaaaaaggat   7080
ctcaagaaga tcctttgatc ttttctacgg ggtctgacgc tcagtggaac gaaaactcac   7140
gttaagggat tttggtcatg agattatcaa aaaggatctt cacctagatc cttttaaatt   7200
aaaaatgaag ttttaaatca atctaaagta tatatgagta aacttggtct gacagttacc   7260
aatgcttaat cagtgaggca cctatctcag cgatctgtct atttcgttca tccatagttg   7320
cctgactccc cgtcgtgtag ataactacga tacgggaggg cttaccatct ggccccagtg   7380
```

-continued ctgcaatgat accgcgagac ccacgctcac cggctccaga tttatcagca ataaaccagc 7440
cagccggaag ggccgagcgc agaagtggtc ctgcaacttt atccgcctcc atccagtcta 7500
ttaattgttg ccgggaagct agagtaagta gttcgccagt taatagtttg cgcaacgttg 7560
ttgccattgc tacaggcatc gtggtgtcac gctcgtcgtt tggtatggct tcattcagct 7620
ccggttccca acgatcaagg cgagttacat gatcccccat gttgtgcaaa aaagcggtta 7680
gctccttcgg tcctccgatc gttgtcagaa gtaagttggc cgcagtgtta tcactcatgg 7740
ttatggcagc actgcataat tctcttactg tcatgccatc cgtaagatgc ttttctgtga 7800
ctggtgagta ctcaaccaag tcattctgag aatagtgtat gcggcgaccg agttgctctt 7860
gcccggcgtc aatacgggat aataccgcgc cacatagcag aactttaaaa gtgctcatca 7920
ttggaaaacg ttcttcgggg cgaaaactct caaggatctt accgctgttg agatccagtt 7980
cgatgtaacc cactcgtgca cccaactgat cttcagcatc ttttactttc accagcgttt 8040
ctgggtgagc aaaaacagga aggcaaaatg ccgcaaaaaa gggaataagg gcgacacgga 8100
aatgttgaat actcatactc ttcctttttc aatattattg aagcatttat cagggttatt 8160
gtctcatgag cggatacata tttgaatgta tttagaaaaa taaacaaata ggggttccgc 8220
gcacatttcc ccgaaaagtg ccacctgacg tc 8252

<210> SEQ ID NO 25
<211> LENGTH: 239
<212> TYPE: DNA
<213> ORGANISM: Artificial
<220> FEATURE:
<223> OTHER INFORMATION: adeno-associated virus/cellular junction

<400> SEQUENCE: 25
tacaggacct ccctaaccct atgacgtaat tcacgtcacg actccttccc tgccctgccc 60
tctcctgaac ctgagccagc tcccatagct cagtctggtc tatctgcctg gccctggcca 120
ttgtcacttt gcgctgccct cctctcgccc ccgagtgccc ttgctgtgcc gccggaactc 180
tgccctctaa cgctgccgtc tctctcctga gtccggacca ctttgagctc tactggctt 239

<210> SEQ ID NO 26
<211> LENGTH: 238
<212> TYPE: DNA
<213> ORGANISM: Artificial
<220> FEATURE:
<223> OTHER INFORMATION: adeno-associated virus/cellular junction

<400> SEQUENCE: 26
tacaggacct ccctaatccc tatgacgtaa ttcacgtcac gactccttcc ctgccctgcc 60
ctctcctgaa cctgagccag ctcccatagc tcagtctggt ctatctgcct ggccctggca 120
ttgtcacttt gcgctgccct cctctcgccc cgagtgccct tgctgtgccg ccggaactct 180
gccctctaac gctgccgtct ctctcctgag tccggaccac tttgagctct actggctt 238

AAV2 REP PROTEIN FUSIONS

CROSS-REFERENCE TO RELATED APPLICATION

This application claims the benefit of U.S. provisional application Ser. No. 60/432,258 filed Dec. 11, 2002.

STATEMENT REGARDING FEDERALLY SPONSORED RESEARCH

This invention was made with government support in the form of grant no. HL60898-01A1 from the United States Department of Health and Human Services, National Institutes of Health, National Heart, Lung, and Blood Institute, and grant no. CA33572 from the Department of Health and Human Services, National Institutes of Health, the National Cancer Institute. The United States Government may have certain rights in the invention.

BACKGROUND OF THE INVENTION

1. Technical Field

This invention relates to the field of molecular biology. In particular, the invention relates to methods and compositions of matter for promoting stable, site-specific integration of Rep-deleted recombinant adeno-associated virus (rAAV) vectors via delivery of a functional AAV Rep gene product to the necessary location by fusing a nucleic acid encoding it to a nucleic acid encoding an intercellular trafficking "cargo" protein such as herpes simplex virus (HSV) tegument protein, VP22 or fragment thereof.

2. Description of the Background Art

Recombinant adeno-associated virus vectors have recently emerged as promising vehicles for gene transfer for a variety of reasons, including their lack of pathogenicity, wide host range, ability to transduce nonproliferating target cells, stable genomic integration, and comparatively low intrinsic immunogenicity. Genetic and sequence analyses of wild type AAV2 have demonstrated two primary open reading frames (ORFs). The left ORF is necessary for virus DNA replication, and contains two promoters at map positions 5 (p5) and 19 (p19). These promoters control expression from colinear, overlapping reading frames that arise from unspliced and spliced transcripts which produce Rep proteins of 78, 68, 52, and 40 kDa respectively. The right ORF, which is necessary for virion encapsulation, contains a single promoter at map position 40 (p40), and encodes three overlapping proteins (VP1, VP2, and VP3) with alternative translational initiation sites. The AAV coding regions are flanked by inverted terminal repeats (ITRs) which possess weak intrinsic promoter activity and are critical for DNA replication, encapsulation and host cell integration. See Berns, in "The Parvoviridae: The Viruses and Their Replication," *Fields Virology*, Fields, Knipe and Howley, Eds., $3^{rd}$ edition, Lippincott-Raven, 1996, pp. 2173–2197; Chatterjee and Wong, "Adeno-associated virus vectors for transduction of genes encoding ribozymes," in *Intracellular Ribozyme Applications: Principles and Protocols*, Rossi and Couture (Eds.), Horizon Scientific Press, 1999; Wong and Chatterjee, "Parvovirus Vectors for Cancer Gene Therapy," in *Cancer Gene Therapy*, Lattine and Gershon, Eds., Academic Press, 2000.

One of the most interesting features of wild type AAV is its ability to integrate into a specific region in human chromosome 19 termed AAVS1. Kotin et al., *Proc. Natl. Acad. Sci. USA*, 87:2211–2215, 1990; Samulski et al., *EMBO J.* 10:3941–3950, 1991. Mutational and deletion analyses have demonstrated that this property is mediated by Rep68/78, the product of the p5 promoter. Surosky et al., *J. Virol.* 71(10):7951–7959, 1997. Theoretically, the capacity to integrate site-specifically would be highly advantageous for rAAV vectors for several reasons. From a safety standpoint, nonrandom integration would lessen the likelihood of insertional mutagenesis. Kung et al., *Curr. Top. Microbiol. Immunol.* 171:1–25, 1991. In addition, cellular sequence flanking inserts are known to affect trans gene expression, resulting in varying levels of expression depending upon the location of insertion. Lacy et al., *Cell* 34(2):343–358, 1983. Targeted vector integration could minimize this variability of expression.

The rep gene has been removed from essentially all currently used rAAV vectors, both to provide a larger space for insertion of recombinant transgenes and to minimize the risks of recombinational events generating wild type AAV during the encapsulation process. Thus, although some studies indicate that integration is not totally random, rep-minus, wild type free rAAV stocks no longer integrate site specifically into AAVS1. Fisher-Adams et al., *Blood* 88:492–504, 1996; Rivadeneira et al., *Int. J. Oncol.* 12(4): 805–810, 1998.

There is a need in the art for methods to improve the potential safety of rAAV vectors and to modify gene expression from rAAV vectors, in particular, methods which would allow site specific integration of rep-deleted rAAV vectors. Delivery of a functional AAV rep gene product to the necessary location would be of great value in achieving safer gene transfer with less unpredictable expression levels. Restoration of site-specific integration of rAAV vectors could significantly impact upon the safety and utility of rAAV vectors for gene transfer and potential gene therapy.

SUMMARY OF THE INVENTION

Accordingly this invention provides a method for mediating site-specific integration of a rep-deleted rAAV vector in a cell, which comprises contacting the cell or expressing in the cell a fusion polypeptide which comprises an AAV2 Rep protein sequence of the left open reading frame of the rep gene that lacks a functional nuclear localization signal (NLS) and a VP22 polypeptide sequence that confers intercellular trafficking on the fusion polypeptide. The Rep protein may be fused at the carboxyl or amino terminus of the VP22 polypeptide and may be fused to it directly or indirectly, via a spacer of one or several amino acids. The AAV Rep protein preferably is truncated to remove amino acid residues 489, 490, 491 or 492 and the remaining carboxyl terminus of the translated Rep protein. The truncation most preferably is located at amino acid 490 or 491. Fusion proteins as described and DNA constructs encoding them also form part of this invention. The invention also provides, in another embodiment, a method of increasing the level of integration of a rAAV vector in a cell comprising contacting the cell with a Rep fusion protein having a mutation in the AAV2 NLS.

BRIEF DESCRIPTION OF THE FIGURES

FIG. 11 presents preliminary DNA sequence alignment analysis of a cell-vector junction sequence isolated following TA cloning of the junction fragment (SEQ ID NOS: 25–26).

DETAILED DESCRIPTION OF THE PREFERRED EMBODIMENTS

Recently, a variety of peptides and proteins, such as the herpes simplex virus tegument protein VP22, have been shown to traffic intercellularly, both as native forms and as fusions with other proteins. See, for example, U.S. Pat. No. 6,251,398. This invention takes advantage of this ability to deliver a functional AAV gene product to cells to promote site specific rAAV integration and gene delivery.

Several peptides and proteins, collectively termed "cargo" proteins, which are capable of trafficking intercellularly have been described. These include the *Drosophila* antennaepedia protein, the HIV-1 tat protein and herpes simplex virus (HSV) tegument protein, VP22. See Schwarze and Dowdy, *Trends Pharmacol. Sci.* 21(2):45–48, 2000. Any known cargo protein is contemplated for use in the invention. Peptides and proteins fused in frame to these cargo proteins also are transported intercellularly, and, most importantly, can retain function. Intercellular transport and nuclear accumulation in vitro have been described with VP22 fused to green fluorescent protein (GFP), the tumor suppressor protein p53, and the herpes simplex virus thymidine kinase suicide gene. Elliott and O'Hare, *Cell* 88(2): 223–233, 1997; Phelan et al., *Nat. Biotechnol.* 16(5):440–443, 1998; Dilber et al., *Gene Ther.* 6(1):12–21, 1999. Analogous studies have been reported for HIV-1 tat fusions with several cell cycle regulatory proteins, including p27Kipl and pl6lNK4a. Nagahara et al., *Nat. Med.* 4(12): 1449–1452, 1998; Gius et al., *Cancer Res.* 59(11):2577–2580, 1999. P-galactosidase fused to HIV-1 tat trafficked widely in an in vivo mouse model. Schwarze et al., *Science* 285(5433):1569–1572, 1999). The exact mechanisms by which these proteins mediate intercellular transport have been difficult to elucidate, although transport mediated by HIV-1 tat appears to be receptor independent, and is more efficient when the tat fusion protein is denatured.

Figure 3B:
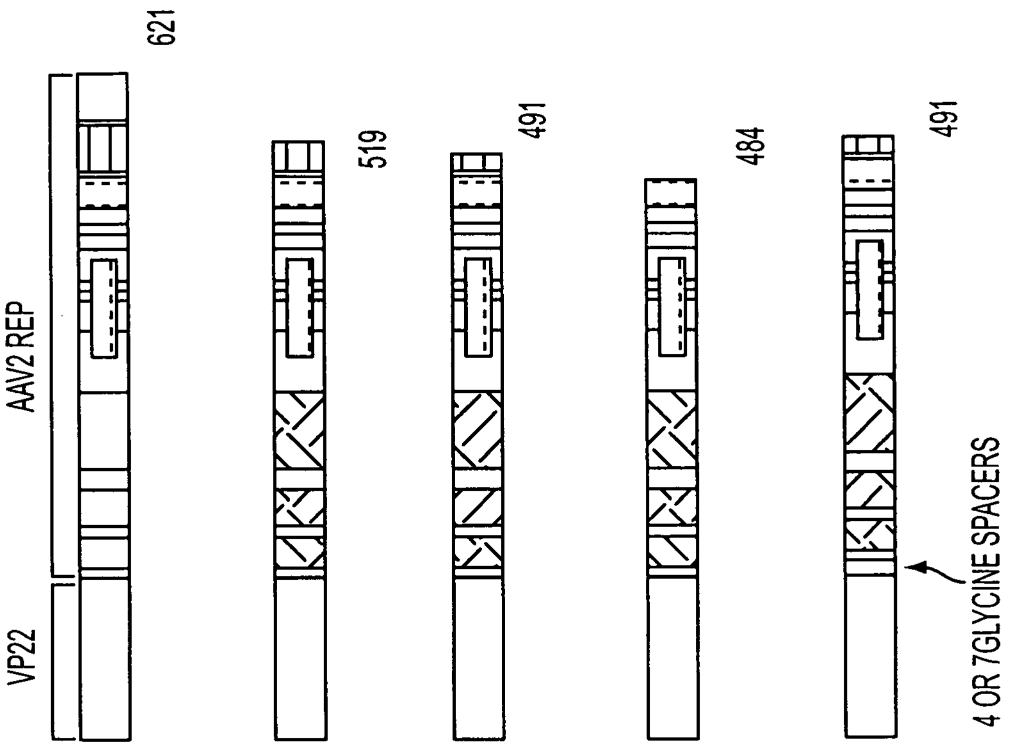
FIGS. 3A and 3B are cartoons showing progressive carboxyl terminal deletions into the AAV2 Rep nuclear localization signal constructed using polymerase chain reaction and fused to the amino terminal portion (3A) or carboxyl terminal portion (3B) of VP22.
Figure 3A:
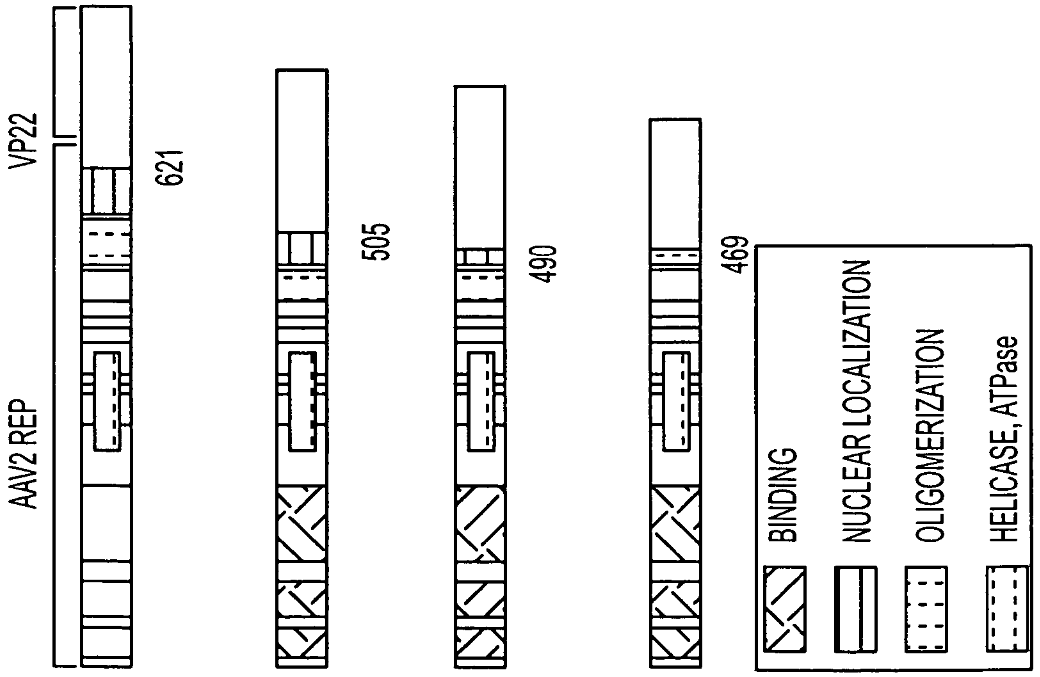

The ability of these cargo proteins to deliver functional genes was used In the present invention to promote site-specific integration of the nucleic acid encoding rAAV and to increase the level of integration, to significantly enhance the potential safety of the gene delivery and to provide an improved method for expression. A variety of exemplary RepVP22 fusion constructs were constructed in which a nucleic acid encoding AAV rep or fragments thereof were linked in frame to a nucleic acid encoding the N- or C-terminus of VP22 within an expression plasmid (Invitrogen). These constructs were transfected into 293 cells, where protein expression, intercellular trafficking, and Rep function were monitored. These fusion constructs, for example AAV2Rep$_{490}$VP22, VP22(Gly$_4$)-AAV2Rep$_{491}$ and VP22 (Gly$_7$)-AAV2Rep$_{491}$, are considered part of the present invention. See Table Table I, FIGS. 3A and 3B, and SEC ID NOS:21 and 22.

Fusion constructs according to this invention are designed to traffic intercellularly by eliminating interference by the NLS present in AAV2 Rep. The AAV2 Rep NLS extends from amino acids 485–519 of the translated Rep ORF. A mutation in or truncation of the gene which deletes all or part of the NLS such that the NLS function is lost restores trafficking ability. Thus, according to the invention, genes truncated or otherwise mutated to remove the protein's ability to signal for nuclear localization are useful to deliver any desired gene and to promote high levels of site-specific integration of the gene and improve expression qualitatively and quantitatively. Therefore, any fusion polypeptide or DNA construct encoding such polypeptide having these properties may be used in the present invention.

Any polypeptide sequence that confers nuclear localization on the fusion polypeptide, as known in the art, may be used with the inventive compositions and methods. For example, VP22 polypeptides or fragments or variants thereof which retain the desired nuclear localization function are preferred. Other polypeptides suitable for use in these inventive fusion polypeptides include *Drosophila* antennaepedia protein, HIV-1 tat protein and functional fragments or variants thereof. Functional segments of the polypeptide, whether truncated at the carboxyl or amino terminus, or both or internal deletions are included in the term fragment. The term variant includes polypeptides containing amino acid substitutions, whether conservative or not, which are at least 80% homologous and preferably 90%, 95% or 99% homologous to the native sequence and which retain the desired nuclear localization function. Persons of skill in the art are well aware of methods of constructing or purifying such molecules and of manipulating them by molecular biological techniques to construct the desired DNA and protein fusions.

Rep protein sequences encoded by the left open reading frame of the AAV2 rep gene that lack a functional nuclear localization signal sequence are suitable for use with the invention. Any such Rep protein sequence may be used, including sequences having a mutation in the NLS which disturbs the NLS function sufficiently to restore trafficking ability. Persons of skill in the art are aware of known methods for determining whether this trafficking ability or the NLS function is present, absent, or sufficiently reduced to allow the inventive methods to operate in the system of choice, using known or routinely modified assays and other techniques. Therefore, any AAV2 Rep protein sequence in which NLS function is absent or severely curtailed (i.e. not detectable or at a level which does not interfere with the functioning of the inventive method) compared to the activity of full-length native Rep protein is contemplated for use with this invention.

Specifically, Rep protein sequences in which the NLS is deleted may be used, for example by deletion of amino acids 485–519 of the native sequence or by truncation of the carboxyl terminal portion of the Rep protein at amino acid 485, amino acid 486, amino acid 487, amino acid 488, amino acid 489, amino acid 490, amino acid 491, amino acid 492, amino acid 493 or amino acid 494. By truncation at an amino acid residue, it is indicated that the amino acids carboxyl terminal to the named amino acid are removed. For example, in a protein truncated at amino acid 491, the carboxyl terminal residue of such a protein would be amino acid 491. Any deletions of the NLS which disturb function as described above may be used. For example deletion of amino acids 485–519 or 486–518 or 489–492 are suitable. Persons of skill in the art consider it routine to construct a variety of such deletion mutants and/or truncations of proteins. Therefore, such variations are considered part of the inventive compositions and methods. Rep protein mutants having point mutations in the NLS also may be used, as well as Rep protein sequences in which all or part of the NLS sequence has been removed and replaced with non-functional spacer amino acid residues.

TABLE I

Description of Exemplary RepVP22 DNA Constructs.

| CONSTRUCT | DESCRIPTION |
|---|---|
| AAV2Rep$_{490}$VP22 | AAV2Rep truncated at amino acid 490 and fused in frame to the amino terminal end of VP22 |
| VP22(Gly)$_4$AAVRep$_{491}$ | AAV2Rep truncated at amino acid 491 and fused in frame to the carboxyl terminal end of VP22 with DNA encoding 4 glycine residues separating the two open reading frames |
| VP22(Gly)$_7$AAVRep$_{491}$ | AAV2Rep truncated at amino acid 491 and fused in frame to the carboxyl terminal end of VP22 with DNA encoding 7 glycine residue separating the two open reading frames |

Figure 5:
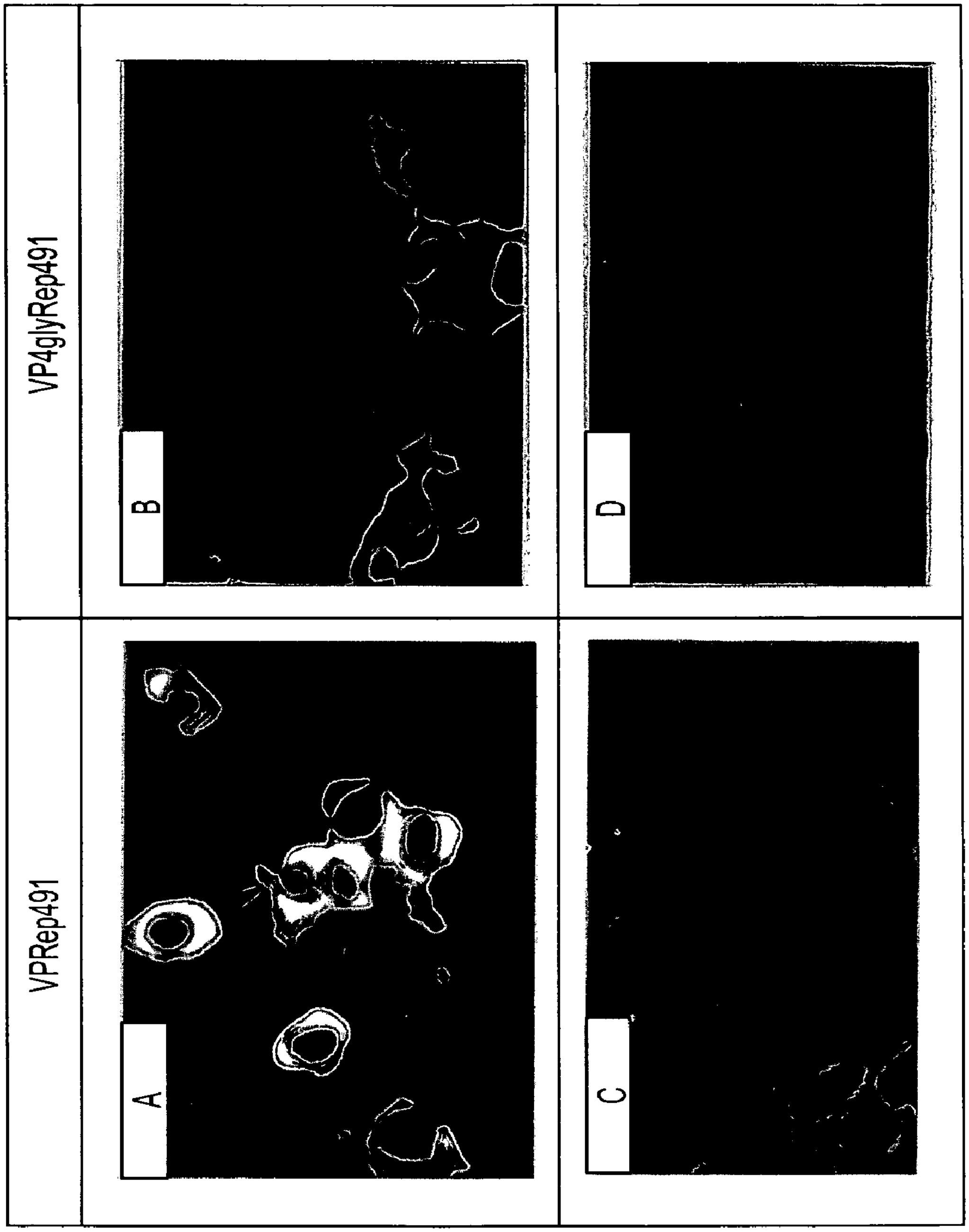
FIG. 5 is a series of immunofluorescence stains for fusion protein (A and B) and for DAPI (C and D).

Western analysis demonstrated that all RepVP22 constructs were expressed as stable protein products of expected size. Protein expressed from full length rep fused to VP22 did not traffic intercellularly (data not shown). A protein encoded by a fusion gene truncated at the nucleotides encoding amino acid 490 of the AAV2 rep gene product did traffic intercellularly as assessed by immunofluorescence microscopy and flow cytometry. See, for example, FIG. 7. In this construct, Rep$_{490}$-VP22, the rep open reading frame, truncated at amino acid residue 490 of the translated Rep protein, was fused in frame to DNA encoding the amino terminal end of VP22. Interestingly, an analogous VP22-Rep$_{491}$ fusion protein did not traffic. Insertion of DNA encoding 4 and 7 glydine spacers to separate the VP22 and Rep$_{491}$ domains and circumvent potential steric hindrance to intercellular trafficking restored the ability to traffic intercellularly. See FIG. 5. One of skill in the art will readily recognize that any amino acid residue may be used as a spacer provided that the goal of reducing steric hindrance can be achieved. Therefore, spacer amino acids with small side groups are preferred.

Figure 8A:
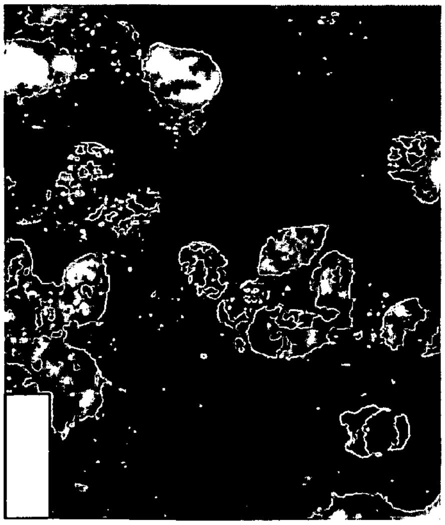
FIGS. 8A and 8B are a pair of photomicrographs of 293 cells stained with a fluorescein isotriocyanate (FITC)-conjugated antibody directed against the recombinant VP22 (Gly)$_7$AAV2Rep$_{491}$ protein showing VP22(Gly)$_7$AAV2Rep$_{491}$ trafficking (A) and a DAPI stain to show all cells in the field (B)
Figure 8B:
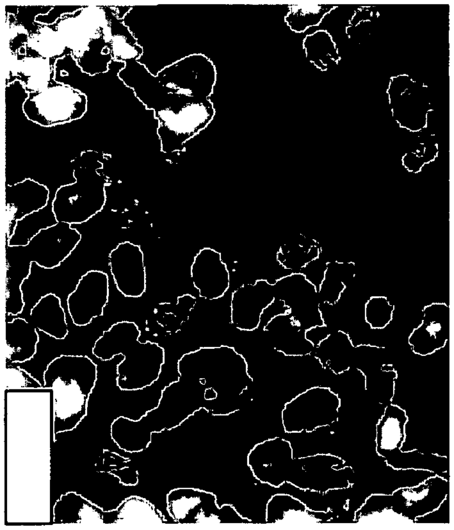
Figure 9:
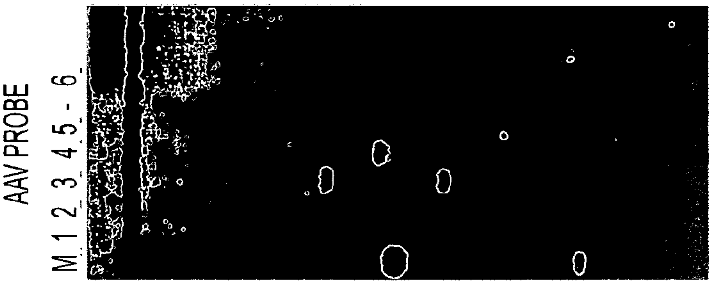
FIG. 9 is a Southern blot probed with an rAAV-specific probe (lane 1: 293 only; lane 2: Apap+VP22(Gly)$_7$AAV2Rep$_{491}$, #2; lane 3: Apap+VP22(Gly)$_7$AAV2Rep$_{491}$, #13; lane 4: Apap+VP22(Gly)$_7$AAV2Rep$_{491}$, #16; lane 5: Apap+VP22(Gly)$_7$AAV2Rep$_{491}$, #33; lane 6: 7374).
Figure 10:
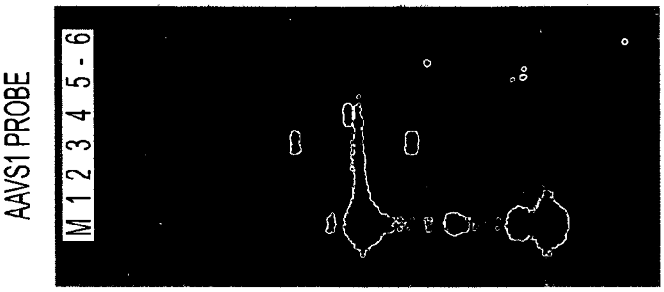
FIG. 10 is a Southern blot probed with an AAVS1-specific probe (lane 1: 293 only; lane 2: Apap+VP22(Gly)$_7$AAV2Rep$_{491}$, #2; lane 3: Apap+VP22(Gly)$_7$AAV2Rep$_{491}$, #13; lane 4: Apap+VP22(Gly)$_7$AAV2Rep$_{491}$, #16; lane 5: Apap+VP22(Gly)$_7$AAV2Rep$_{491}$, #33; lane 6: 7374).

A PCR assay which specifically detects vector integration into AAVS1, coupled with Southern analyses, suggested that all three constructs described in Table I promoted site specific rAAV2 vector integration. See FIGS. 8–10. These types of constructs therefore form the basis of a strategy to improve both the safety and efficacy of rAAV vectors.

To confirm integration of the nucleic acid encoding rAAV into the AAVS1 site by Rep$_{490}$VP22, PCR products containing vector-cell junction fragments were cloned and sequenced. See FIG. 11. Fusion proteins were constructed with His tags to facilitate their isolation and purification. The fusion proteins were assessed for their ability to promote site specific integration of the nucleic acid encoding rAAV by simply applying them to cells in the form of purified Rep-VP22 fusion proteins.

To exploit the ability of the fusion cargo proteins to deliver functional protein domains intercellularly, the wild type and several modified AAV2 Rep gene constructs were fused in frame to the nucleic acid encoding VP22 ORE both in amino- and carboxyl-terminal orientations. The fusion proteins were expressed using the highly active CMV IE promoter. Although fusions of VP22 with full length AAV2 Rep did not appear to traffic, specific Rep fusion proteins in which the NLS was truncated, for example VP22(Gly$_7$)-AAV2Rep$_{491}$, trafficked intercellularly and were capable of promoting site specific integration of recombinant RAAV vectors. See FIG. 8.

Fusion proteins according to the invention can be expressed by plasmid DNA transfection according to any method known in the art, including calcium phosphate coprecipitation, for example. Once expressed, the fusion proteins traffic to surrounding cells via the VP22 or other intercellular trafficking protein moiety, and can mediate rAAV vector site specific integration via the AAV Rep moiety. Those of ordinary skill in the art are familiar with such methods and are able to make modifications as desired depending on the protein fusion and cell type(s) involved. Alternatively, fusion proteins can be expressed within cells by introducing expression plasmid DNA via physical methods (lipofection, electroporation, etc.) or by using a viral vector. In addition, purified fusion protein may be applied directly to cells to promote site-specific rAAV vector integration. Because the constructs preferably express fusion proteins with His tags (which allow easy purification by nickel column chromatography) the proteins may be purified after production in bacteria or eukaryotic cells, and then applied directly to cells at the time of rAAV vector transduction. This increases the frequency of rAAV vector integration.

REFERENCES

The references listed below are hereby incorporated into the specification by reference.

1. Aints et al., "Intercellular spread of GFP-VP22." *J. Gene Med.* 1(4):275–9, 1999.
2. Berns, in "The Parvoviridae: The Viruses and Their Replication," *Fields Virology*, Fields, Knipe and Howley (Eds) 3d Edition, Lippincott-Raven, 1996. pp 2173–2197.
3. Brewis et al., "Evaluation of VP22 spread in tissue culture." *J. Virol.* 74(2):1051–6, 2000.
4. Chatterjee et al., "Dual target inhibition of HIV-1 in vitro by means of an adena-associated virus antisense vector." *Science* 258:1485–1488, 1992.
5. Chatterjee et al., "Transduction of primitive human marrow and cord blood-derived hematopoietic progenitor cells with adeno-associated virus vector." *Blood* 93:1882–94, 1999.
6. Chatterjee and Wong, "Adeno-associated Virus Vectors for Transduction of Genes Encoding Ribozymes," *Intra-*

*cellular Ribozyme Applications: Principles and Protocols*, Rossi and Couture (Eds.), Horizon Scientific Press, 1999.
7. Derer et al., "Direct protein transfer to terminally differentiated muscle cells." *J. Mol. Med.* 77(8):609–13, 1999.
8. Dilber et al., "Intercellular delivery of thymidine kinase prodrug activating enzyme by the herpes simplex virus protein, VP22." *Gene Ther.* 6(1):12–21, 1999.
9. Elliott and O'Hare, "Intercellular trafficking and delivery by a herpesvirus structural protein." *Cell* 88(2):223–233, 1997.
10. Elliott and O'Hare, "Intercellular trafficking of VP22-GFP fusion proteins." *Gene Ther.* 6(1):149–251, 1999.
11. Elliott and O'Hare, "Herpes simplex virus type I tegument protein VP22 induces the stabilization and hyperacetylation of microtubules." *J. Virol.* 72(8):6448–6455, 1998.
12. Elliott and O'Hare, "Cytoplasm-to-nucleus translocation of a herpesvirus tegument protein during cell division." *J. Virol.* 74(5):2131–2141, 2000.
13. Fang et al., "Intercellular trafficking of VP22-GFP fusion proteins is not observed in cultured mammalian cells." *Gene Ther.* 5(10):1420–4, 1998.
14. Fisher-Adams et al., "Integration of adeno-associated virus vector genomes in Human CD34 cells following transduction." *Blood* 88:492–504, 1996.
15. Gius et al., "Transduced pl6INK4a peptides inhibit hypophosphorylation of the retinoblastoma protein and cell cycle progression prior to activation of Cdk2 complexes in late G1." *Cancer Res.* 59(11):2577–2580, 1999.
16. Kotin and Berns, "Organization of adeno-associated virus DNA in latently infected Detroit 6 cells." *Virology* 170(2): 460–7, 1989.
17. Kotin et al., "Site-specific integration by adeno-associated virus." *Proc. Natl. Acad. Sci. USA* 87:2211–2215, 1990.
18. Kung et al., "Retroviral mutagenesis of cellular oncogenes: a review with insights into the mechanisms of insertional activation." *Curr. Top. Microbiol. Immunol.* 171:1–25, 1991.
19. Lacy et al., "A foreign beta-globin gene in transgenic mice: integration at abnormal chromosomal positions and expression in inappropriate tissues." *Cell* 34(2):343–358, 1983.
20. Nagahara et al., "Transduction of full-length TAT fusion proteins into mammalian cells: TAT-p27Kipl induces cell migration." *Nat. Med.* 4(12):1449–1452, 1998.
21. Phelan et al., "Intercellular delivery of functional p53 by the herpesvirus protein VP22." *Nat. Biotechnol.* 16(5): 440–443, 1998.
22. Podsakoff et al., "Stable and efficient gene transfer into non-dividing cells by adeno-associated virus (AAV)-based vectors." *J. Virol.* 68:5656–5666, 1994.
23. Rivadeneira et al., "Sites of recombinant adeno-associated virus integration." *Int. J. Oncol* 12(4):805–810, 1998.
24. Rinaudo et al., "Conditional Site-Specific Integration into Human Chromosome 19 by Using a Ligand-Dependent Chimeric Adena-Associated Virus/Rep Protein." *J. Virol.* 74:281–294, 2000.
25. Samulski et al., "Targeted integration of adeno-associated virus (AAV) into human chromosome 19." *EMBO J.* 10:3941–3950, 1991.
26. Schwarze et al., "In vivo protein transduction: delivery of a biologically active protein into the mouse." *Science* 285(5433):1569–1572, 1999.
27. Schwarze and Dowdy, "In vivo protein transduction: intracellular delivery of biologically active proteins, compounds and DNA." *Trends Pharmacol. Sci.* 21(2):45–48, 2000.
28. Surosky et al., "Adeno-associated virus Rep proteins target DNA sequences to a unique locus in the human genome." *J. Virol.* 71(10):7951–7959, 1997.
29. Wong and Chatterjee, "Parovirus Vectors for the Cancer Gene Therapy," *Cancer Gene Therapy*, Lattime and Gershon (Eds.), Academic Press, 2000.

EXAMPLES

Example 1

AAVS1 Site Specific Integration of rAAV

Plasmids pVP22/myc-His and pVP22/myc-His-2 were obtained from Invitrogen (Carlsbad, Calif.). See FIGS. 1 and 2. The nucleic acid encoding the full length AAV2 rep gene product was amplified by PCR and inserted into the pVP22/myc-His vector as an EcoRV and XbaI fragment. The nucleic acid encoding the AAV2 Rep68/78 open reading frame was amplified from pTZAAV, a pUC-based phagemid containing the full length, infectious AAV2 genome inserted as a Bgl II fragment.

Figure 1:
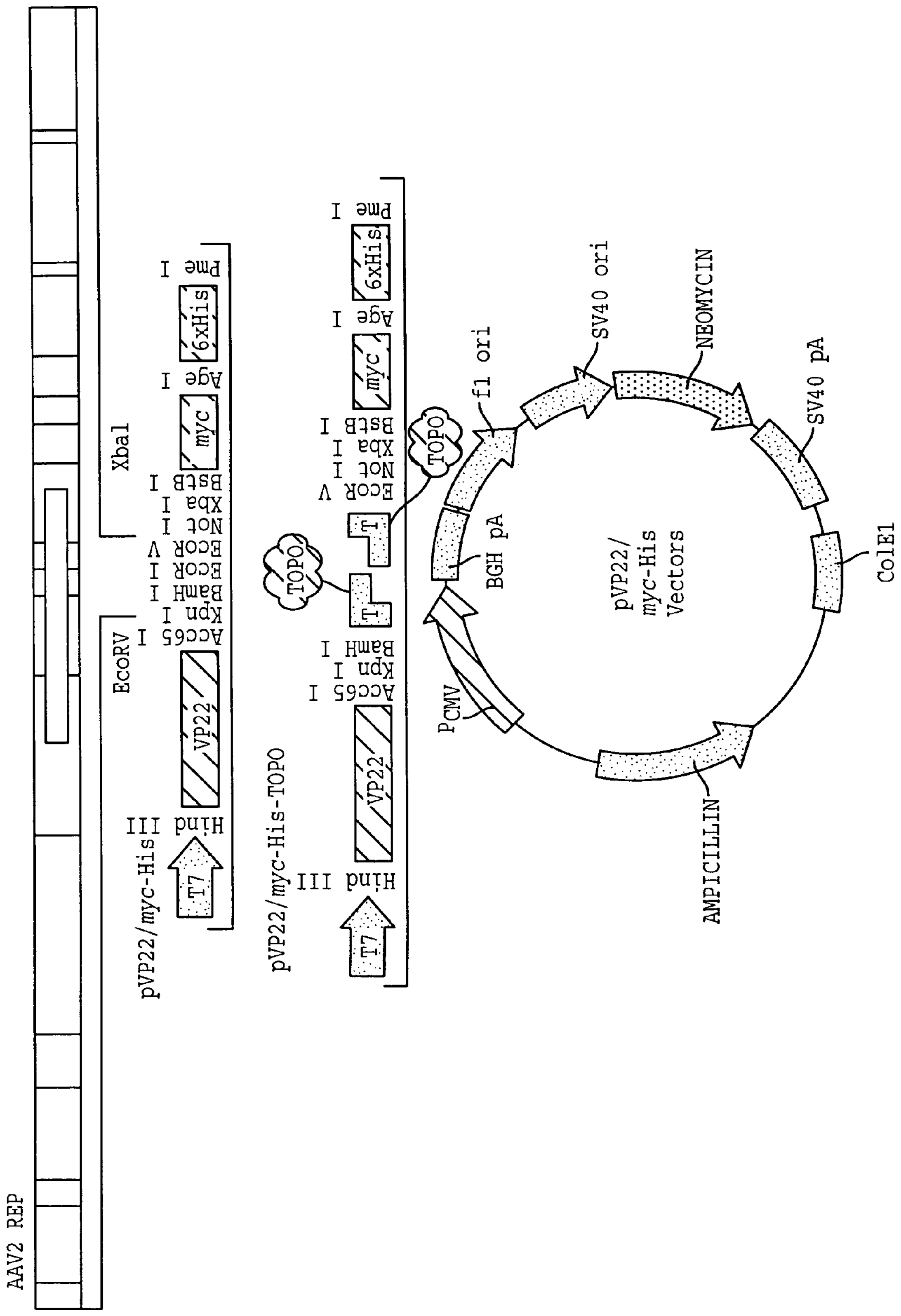
FIG. 1 is a cartoon showing construction of VP22-AAV REP.
Figure 2:
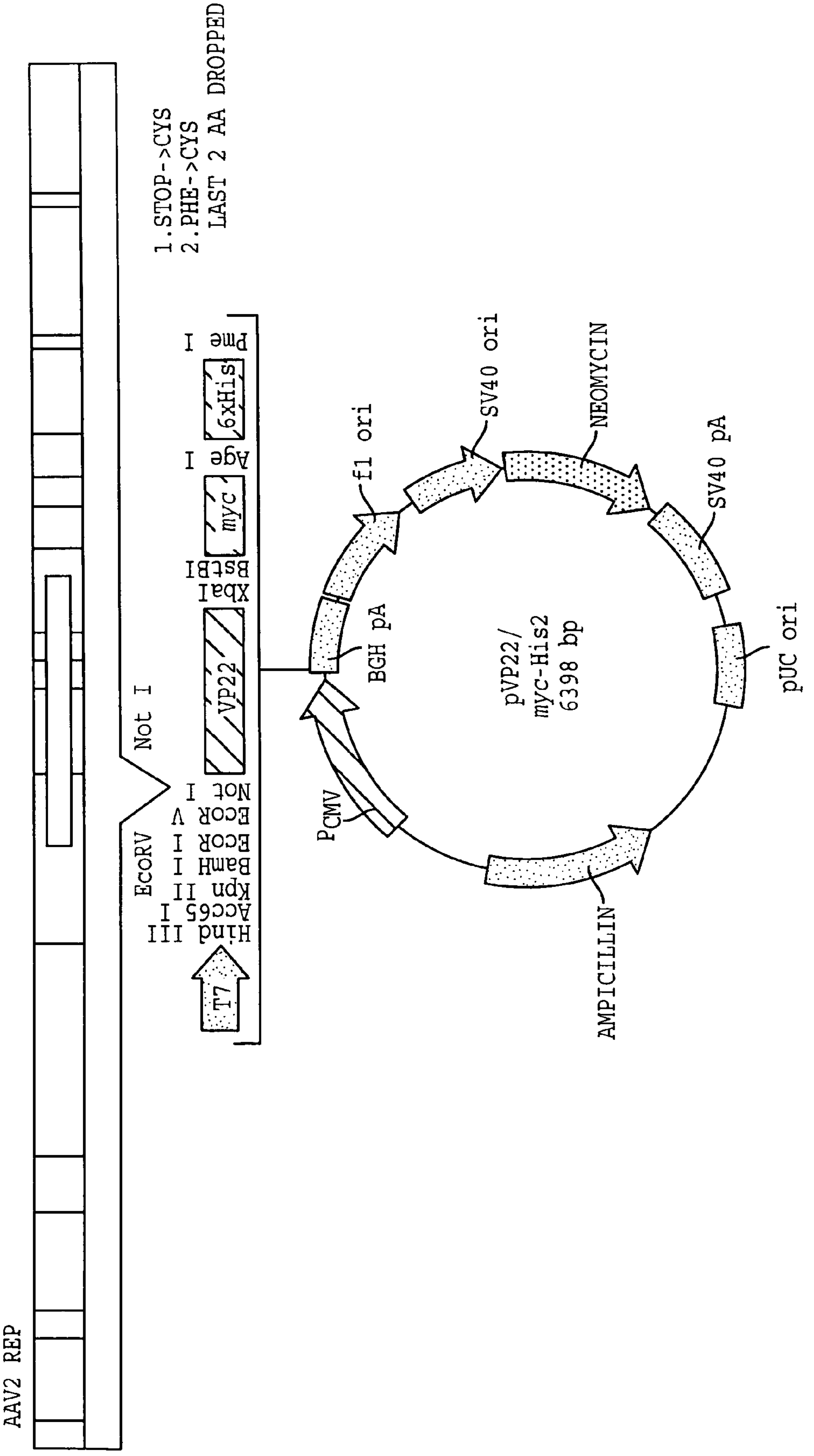
FIG. 2 is a cartoon showing construction of AAV REP-VP22.

To construct a VP22-Rep fusion protein with the full length AAV2 Rep, see FIGS. 1 and 2, the rep gene was amplified as a 1.9 kb fragment using the sense primer 5' GGGAGGTTTGATATCGCAGCCGCCATGCCGGGG 3' (SEQ ID NO:1) with incorporation of an Xba I site (bold) and the antisense primer 5' GATTTAATCTAGATATTGTTCAAAGATGCAG 3' (SEQ ID NO:2) with incorporation of an Xba I site (bold). The rep mRNA stop codon was modified from TAA to TAT as a part of the Xba I site to permit read-through incorporation of myc and His tags at the 3' end of the fusion protein.

The 5'-PCR primer used for the construction of the nucleic acid encoding the full length Rep-VP22 fusion protein was 5' GGTTTGAACGCGCAGATATCATGCCGGGG 3' (SEQ ID NO: 3) which incorporated an EcoRV site (bold). Two different full length Rep-VP22 nucleic acid constructs were made: (1) RepVP22cys, in which the stop codon of the Rep mRNA was modified to a Cysteine residue to allow read-through of the nucleic acid encoding VP22 and (2) RepVP22phe, in which the nucleotides encoding amino acids 620 and 621 were eliminated and the nucleotides encoding residue 619 were modified from nucleotides encoding phenylalanine to nucleotides encoding cysteine to allow for read-through of the nucleic acid encoding VP22. The downstream primer for the RepVP22cys construct was 5' GCCATACCTGATTTAGCGGCCGCATTGTTCAAAGATG 3' (SEQ ID NO: 4), while the downstream primer used to generate the RepVP22phe protein was 5' GATTAAAATCATTTAGCGGCCGCAGATGCAGTCATCCAAA 3' (SEQ ID NO: 5). Both primers incorporated a Not I site (bold) for cloning purposes. See FIG. 3.

Fusion proteins containing progressive carboxyl terminal deletions into the AAV2 NLS protein were expressed from corresponding nucleic acids encoding the proteins with the terminal deletions. Polymerase chain reaction was used to fuse the nucleic acids encoding these terminally deleted AAVs NLS proteins to the nucleic acid encoding the amino terminal portion (FIG. 3A) or the nucleic acid encoding the carboxyl terminal portion (FIG. 3B) of VP22. Initial studies indicated that the $AAV2REP_{490}VP22$ fusion protein trafficked between cells, but that the corresponding VP22-AAV2REP$_{491}$ did not. To circumvent possible steric interference with trafficking, nucleotides encoding 4 and 7 glycines were inserted in frame in the mRNA between the VP22 and AAV2REP$_{491}$ open reading frames. All constructs were sequenced to ensure that no mutations were inadvertently introduced following PCR amplification.

The full-length AAV Rep fusion protein constructs were tested for their ability to traffic intercellularly as follows. 293 or COS cells were transfected with expression plamids encoding the fusion constructs and serially examined for spread of the fusion protein using indirect immunofluorescent microscopy after staining with an antibody directed against the myc tag common to all the fusion proteins. The constructs containing the full length AAV2 Rep did not traffic.

pVP22-Rep constructs that coded for truncations in the NLS protein were constructed in a similar fashion to the previously described full length rep constructs. Nucleic acids encoding Rep proteins truncated at the carboxyl end at amino acids 484 (VP22AAVRep$_{484}$), 491 (VP22AAVRep$_{491}$), and 519 (VP22AAVRep$_{519}$) were generated by PCR cloning. For these modified proteins, the 5' end of the rep mRNA open reading frame was amplified with the same sense primer as VP22-Rep (5' GGGAG-GTTTGATATCGCAGCCGCCATGCCGGGG 3'; SEQ ID NO: 1) and incorporated an EcoRV site (bold). The 3' end of the Rep mRNA ORE for 484, 491 and 519 truncations were amplified with antisense primers, 5' GGCTCCAC-CCTTTTTGTCTAGAAATTCATGCTCCAC 3' (SEQ ID NO: 6), 5' GGGGGCGGGTCTTTCTAGAGCTCCAC-CCTTTTTG 3' (SEQ ID NO: 7), and 5' GTTGATC-GAAGCTTCTAGATCTGACGTCGATGG 3' (SEQ ID NO: 8), respectively, all of which incorporated an Xba I site (bold).

For VP22(Gly)$_4$AAVRep$_{491}$ and VP22(Gly)$_7$AAVRep$_{491}$ constructs, the 5' end of Rep mRNA ORE was amplified with 5' CCATTTTGAAGCGATATCGGTGGAGGCG-GAGCCGCCATGCCGGGG 3' (SEQ ID NO:9) and 5' GGGTCTCCATTTGATATCGGGGGGGGTG-GAGGCGGAGGCGCCATGCCGGGG 3' (SEQ ID NO:10), respectively. EcoRV sites are in bold while bases encoding the glycine spacer residues are in bold and italicized. For the 3' end, the antisense primer for the pVP22-Rep491 mRNA SEQ ID NO:7) was used. The amplified products were digested with EcoRV and XbaI, and inserted into similarly digested pV22/myc-His. Two nucleic acid constructs encoding full-length RepVP22 protein and three nucleic acid constructs encoding truncated RepVP22 protein were generated.

Three nucleic acid constructs encoding truncated Rep proteins, AAVRep$_{469}$VP22, AAVRep$_{490}$VP22 and AAVRep$_{505}$VP22, were created using independent Not I site-containing downstream primers coupled with the identical primer used to generate the full-length construct. The AAVRep$_{469}$VP22 3' primer, 5' GATCCTTTGCCCAGCG-GCCGCCAGTCTTTGACTTCCTGCTTGG 3' (SEQ ID NO:11) extended from +1385 to +1425 with base changes at +1405 to +1408 and +1412. These sequence changes in the primer modified residue 469 of the expressed protein from a phenylalanine to a cysteine and eliminated the production of all amino acids C-terminal to residue 469.

AAVRep$_{490}$VP22 C-terminal primer, 5' GGTCTTTTGCGGCCGCCACCCTTTTTG 3' (SEQ ID NO:12), extended from +1457 to +1483. Mismatches at +1469, +1471, and +1473 to +1475 were used to eliminate all residues C-terminal to 490 in the expressed protein.

AAVRep$_{505}$VP22 3' primer, 5' GACTCGCGCACGCGGC-CGCGCTCACTTATATCTGCG 3' (SEQ ID NO:13), extended from +1496 to +1531. It contained nucleotide changes at positions +1513, +1515 to +1517 and +1520 resulting in the loss of amino acids C-terminal to residue 505 in the expressed protein. Additionally, residue 505 in the expressed protein was modified from a proline to an arginine. All C-terminal primers above are given in the reverse orientation. Not I sites are indicated in bold.

The sequence of the Rep$_{491}$ truncated protein ends at amino acid 491 of the translated Rep protein, however there are 8 amino acids intervening between the C-terminal of the Rep$_{491}$ truncated protein and the initial amino acid of the VP22 polypeptide sequence. These amino acids (DIQH-SGGR; SEQ ID NO:14) result from the expression of additional nucleotides found within the multiple cloning site in the vector. Therefore, it is clear to one of ordinary skill that multiple variations of the fusion peptides are possible, depending on the exact construction methods used to create them. The two moieties of the fusion polypeptide may be fused directly or indirectly, with additional amino acids present at the junction or either terminus. See Table II, below for exemplary sequences contained in the Rep fusion polypeptides compared to Rep wild type. All constructs were analyzed by DNA sequencing to insure that no additional mutations were inadvertently incorporated during the PCR amplifications. See SEQ ID NOs: 21–24 and Table I for sequence information for exemplary constructs.

TABLE II

Sequence Comparison: Wild Type Rep and Truncated Rep-VP22.

| Name | Sequence | SEQ ID NO: |
|---|---|---|
| A. Rep 78 WT | CDLVNVDLDDCIFEQ (607–621) | 15 |
| Rep 78-Cys-VP22 | CDLVNVDLDDCIFEQCGR-VP22 | 16 |
| B. Rep 78 WT | YVKKGGAKKRPAPSD (485–499) | 17 |
| Rep$_{491}$VP22 | YVKKGGADIQHSGGR-VP22 | 18 |
| C. Rep 78 WT | PAPSDADISEPKR (495–507) | 19 |
| Rep$_{505}$VP22 | PAPSCADISERGR-VP22 | 20 |

All rep gene inserts were amplified using a PE 9600 thermal cycler (Perkin and Elmer). A standard 100 μl reaction contained 100 ng of template DNA, 25 pmol of each respective upstream and downstream primer, 2 units of Vent polymerase (New England Biolabs, Beverly, Mass.), 200 μM of each dNTP, 3 mM $MgSO_4$, and 1× Vent reaction buffer. The mixture was denatured at 95° C. for 5 minutes, and then 25 cycles of amplification (95° C., 30 s; 60° C., 30 s; 72° C., 90 s) were performed, followed by one extension cycle at 72° C. for 7 minutes. PCR products were gel purified using the Prep-a-Gene™ purification kit (Bio-Rad Laboratories, Hercules, Calif.), digested with appropriate restriction enzymes (NEB) and ligated into corresponding vectors at 16° C. for 16 hours. Plasmid constructs were transformed into chemically competent DH5a cells using standard methods. Plasmids were purified by anion exchange column chromatography (Qiagen, Valencia, Calif.), and quantitated spectrophotometrically. Enzymes were used according to conditions suggested by the manufacturers. Oligonucleotides were synthesized using a 394 B DNA Synthesizer (Applied Biosystems, Foster City, Calif.). All constructs were sequenced to insure that mutations were not inadvertently introduced during amplification.

Figure 12:
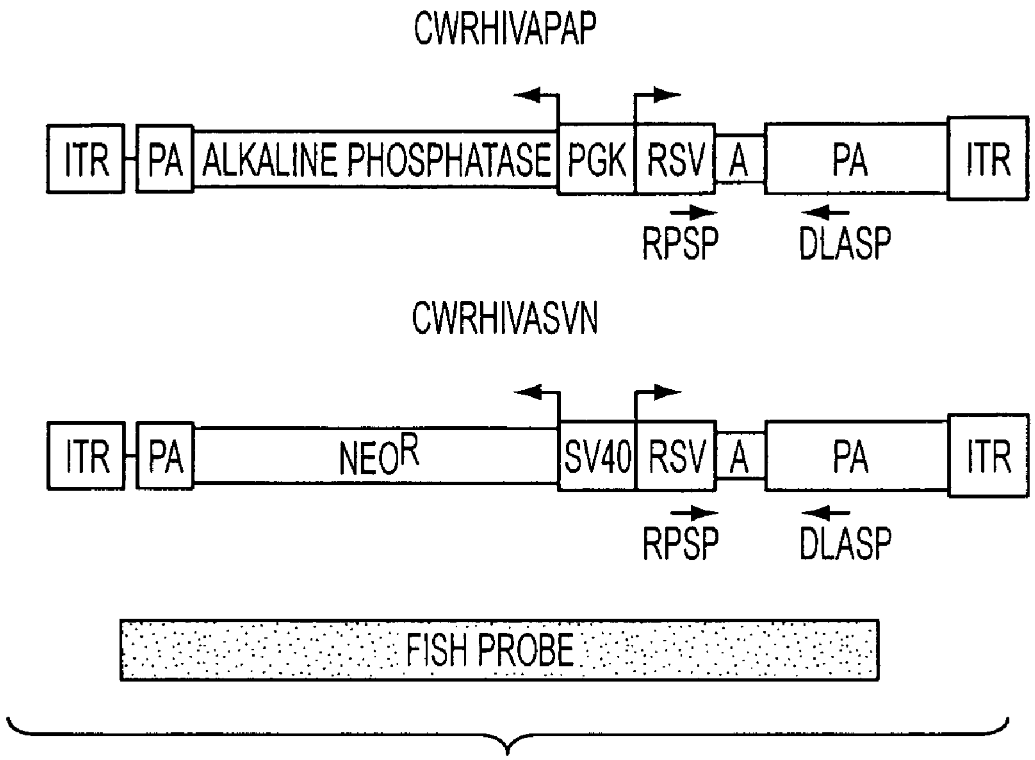
FIG. 12 shows a map of CWRHIVAPAP.

FIG. 12 shows a map of CWRHIVAPAP. This construct contains one expression cassette encoding an antisense RNA complementary to the HIV TAR region under RSV LTR control, and another cassette encoding an antisense RNA complementary to the hu-placental alkaline phosphatase (hu PLAP) under PGK promoter control. CWRPGKH is similar to CWRHIVAPAP except for substitution of a PGK hygromycin resistance cassette for the PGK PLAP cassette.

Figure 4:
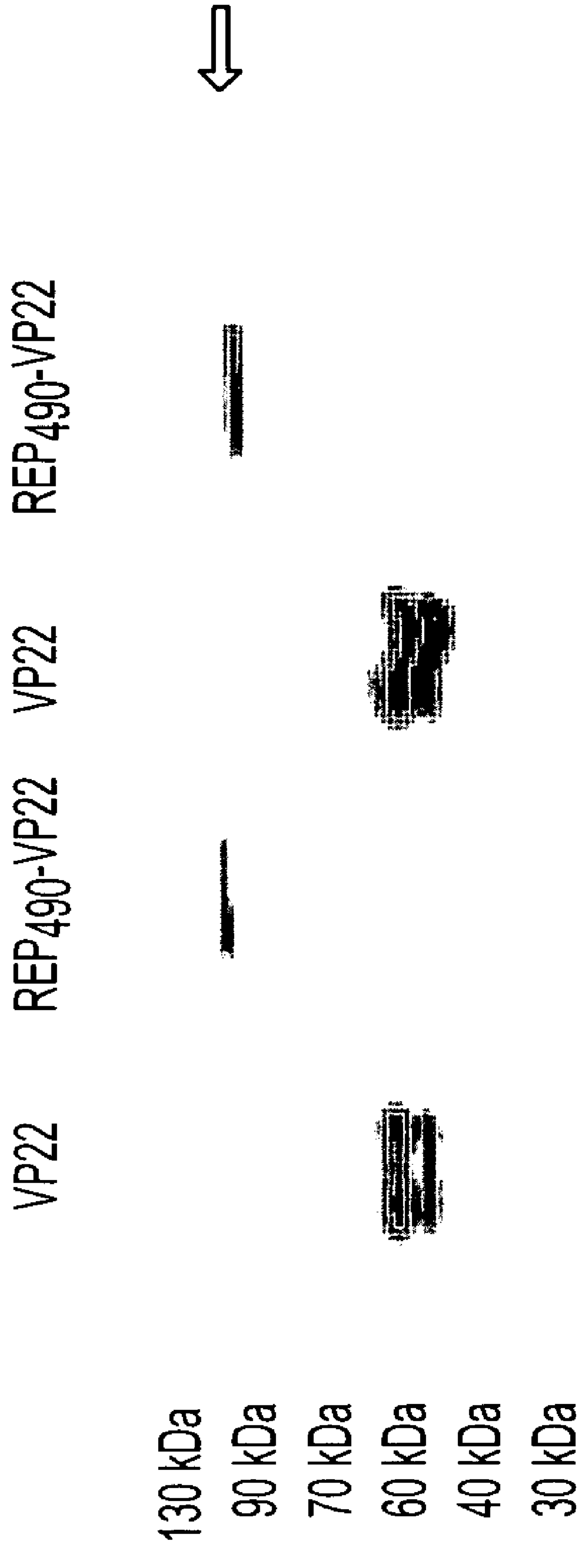
FIG. 4 shows a western blot demonstrating expression of the AAVRep$_{490}$VP22 fusion protein following transfection.

African green monkey Vero (#CCL-81) cells, 293 cells, COS cells and a Detroit 6-derived cell line, 7374, which contains integrated wild type AAV2, were maintained in high glucose Dulbecco's MEN (DMEM) with 2 mM glutamine and 10% heat inactivated fetal calf serum, at 37° C. in 5% humidified $CO_2$. All cells were routinely tested and found free of mycoplasma. All transfections were performed using a CellPhect Transfection kit (calcium phosphate procedure; Amersham Pharmacia, Piscataway, N.J.) according to the manufacture's directions. For Western blot of VP-Rep fusion proteins, 293 cells were transfected with VP22-Rep or Rep-VP22 constructs (or their associated modified constructs lacking a functional NLS) using calcium phosphate coprecipitation. Cells were harvested after 48 hours and lysed. Proteins were separated using SDS-PAGE electrophoresis, and transferred to nitrocellulose. The western analyses demonstrated expression of the $AAVREP_{490}V22$ fusion protein following transfection. See FIG. 4.

Example 2

Rep Expression and Trafficking Analyses by Immunofluorescence Microscopy

Amino and carboxyl-terminal VP22/AAV2 Rep fusion proteins encoded by expression plasmids were initially tested for their ability to traffic intercellularly after calcium-phosphate transfection into 293 cells. For immunofluorescence assays, approximately $6.0\times10^5$ 293 cells were plated on coverslips in 6-well plates and transfected with 1–3 μg of expression vector DNA for the various Rep derivatives. At specified times post-transfection, cells were briefly washed 3 times in room temperature phosphate-buffered saline (PBS), fixed in methanol at −20° C. for 5 minutes, and permeabilized by incubating them in acetone for 2–5 minutes at −20° C. The fixed cells were subsequently blocked with 1% BSA/1×PBS for 5 minutes at room temperature and stained with 1 μM primary mouse monoclonal anti-rep (such as CAT# MAB6030, Maine Biotechnology, Portland, Me.) or anti-c-myc antibody (such as CAT# R950-25, Invitrogen) diluted in 1% BSA/1×PBS, for 1 hour. The cells were then washed 3 times in PBS, 5 minutes each time, and incubated for 1 hour with a FITC-conjugated goat anti-mouse IgG secondary antibody (such as CAT# sc-2010; Santa Cruz Biotechnology, Santa Cruz, Calif.) and DAPI (4', 6-diamidino-2-phenylindole; Sigma, St. Louis, Mo.). Following the washes, the fixed cells were briefly rinsed in sterile $dH_2O$, air-dried, and mounted onto glass slides using a 50% glycerol in $dH_2O$. All staining procedures were conducted at room temperature. Cells were photographed by epifluorescense on a Nikon Labophot-2 photomicroscope with fluorescein and DAPI filters using a Nikon Fluor 40× objective. No visible staining of the full length RepVP22 protein was seen outside of the nucleus. Therefore, it appears that Rep-NLS overrides VP22's inherent nature to traffic outside of cell.

The ability of $VP22AAV2Rep_{491}$ and VP22(Gly)$_4$AAV2$Rep_{491}$ proteins to traffic intercellularly also were compared following transfection. Cells were stained for fusion protein with fluorescein isothiocyanate CFITC) and with 4'-6-diamidino-2-phenylindole-2HCl (DAPI) to visualize the cells. See FIG. 5. Panels 5A and 5B show immunofluorescent staining indicating the presence of the fusion protein. The results indicate that the 4-glycine insert protein traffics intercellularly.

Example 4

Flow Cytometry

Figure 6A:
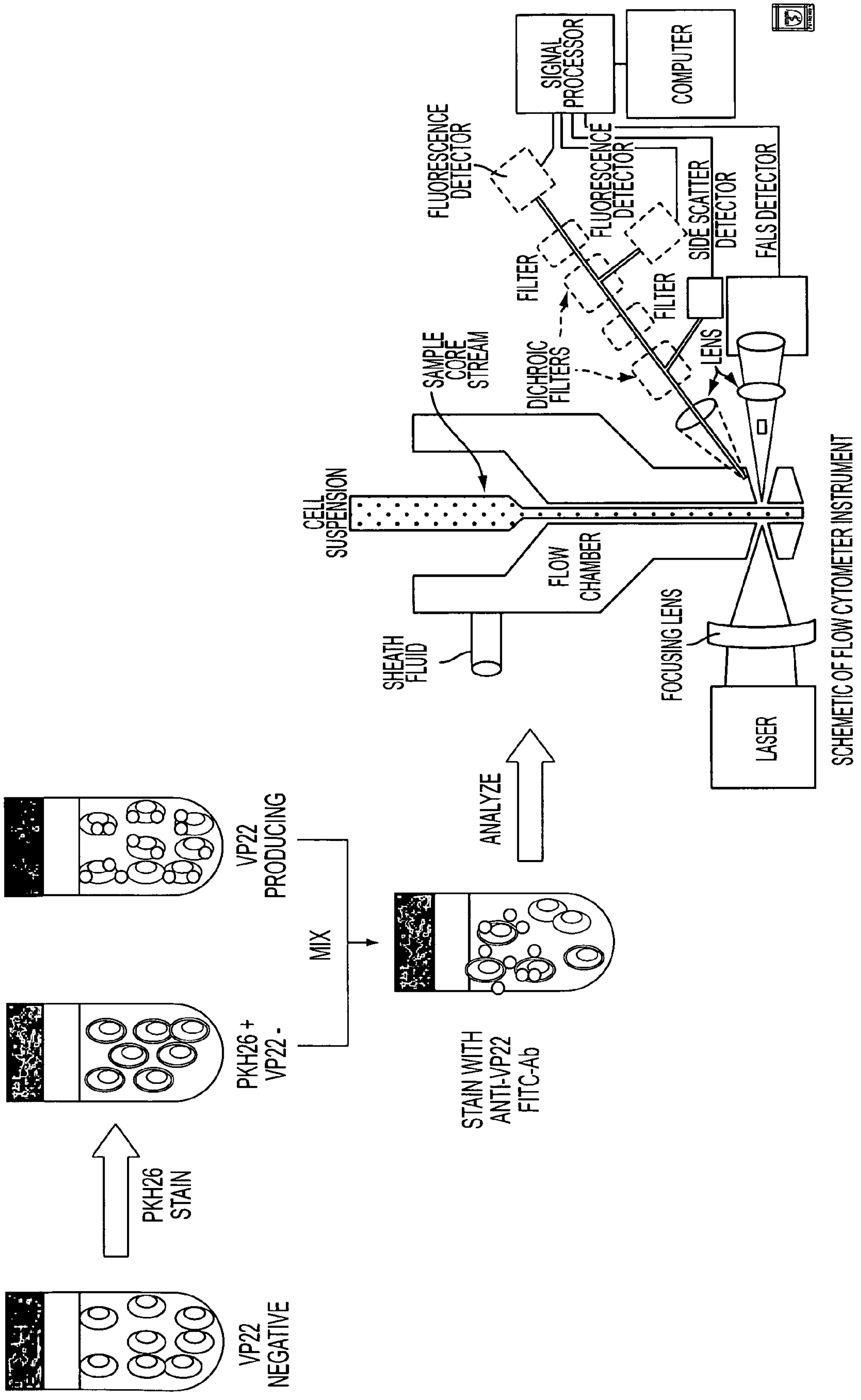
FIG. 6A is a flow chart showing the scheme for the analysis of intercellular protein trafficking using flow cytometry.
Figure 6B:
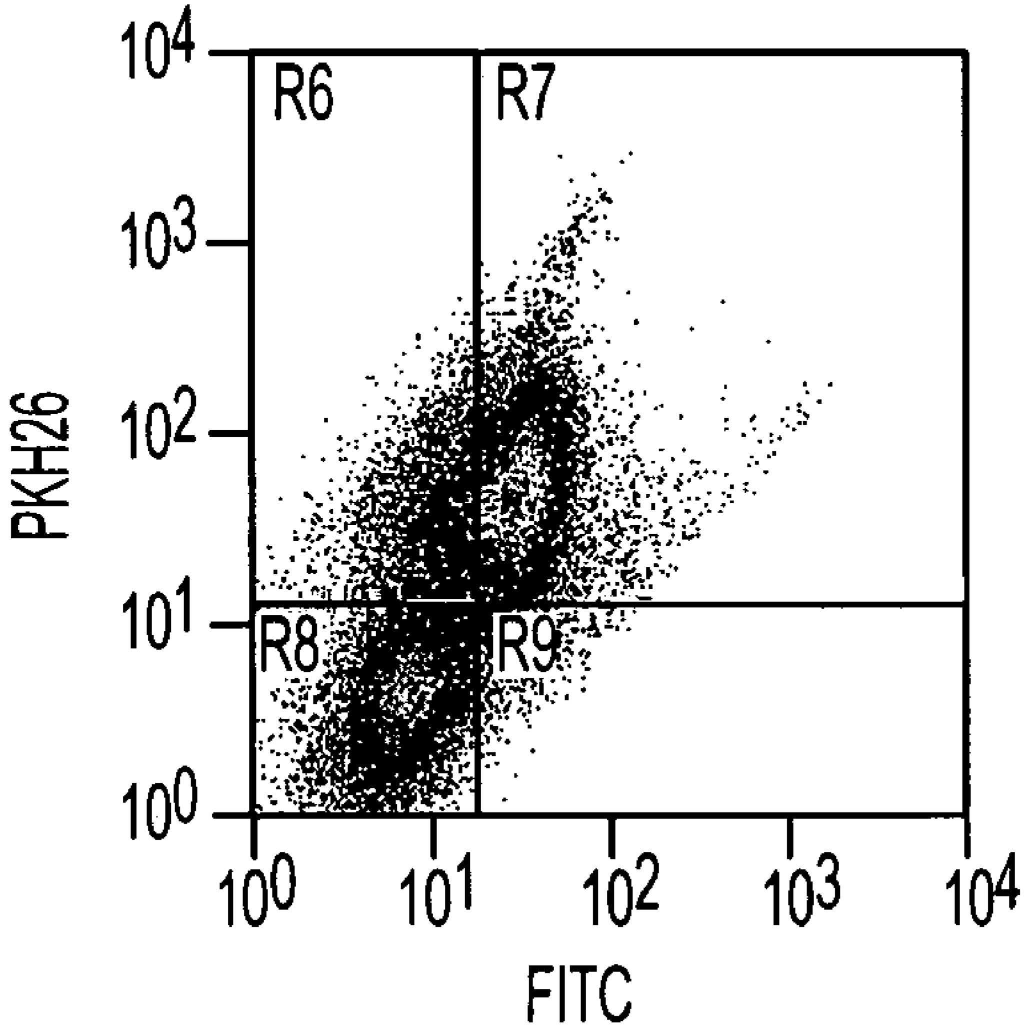
FIG. 6B shows results of the flow cytometry analysis.
Figures 7A, 7B, 7C, 7D, 7E:
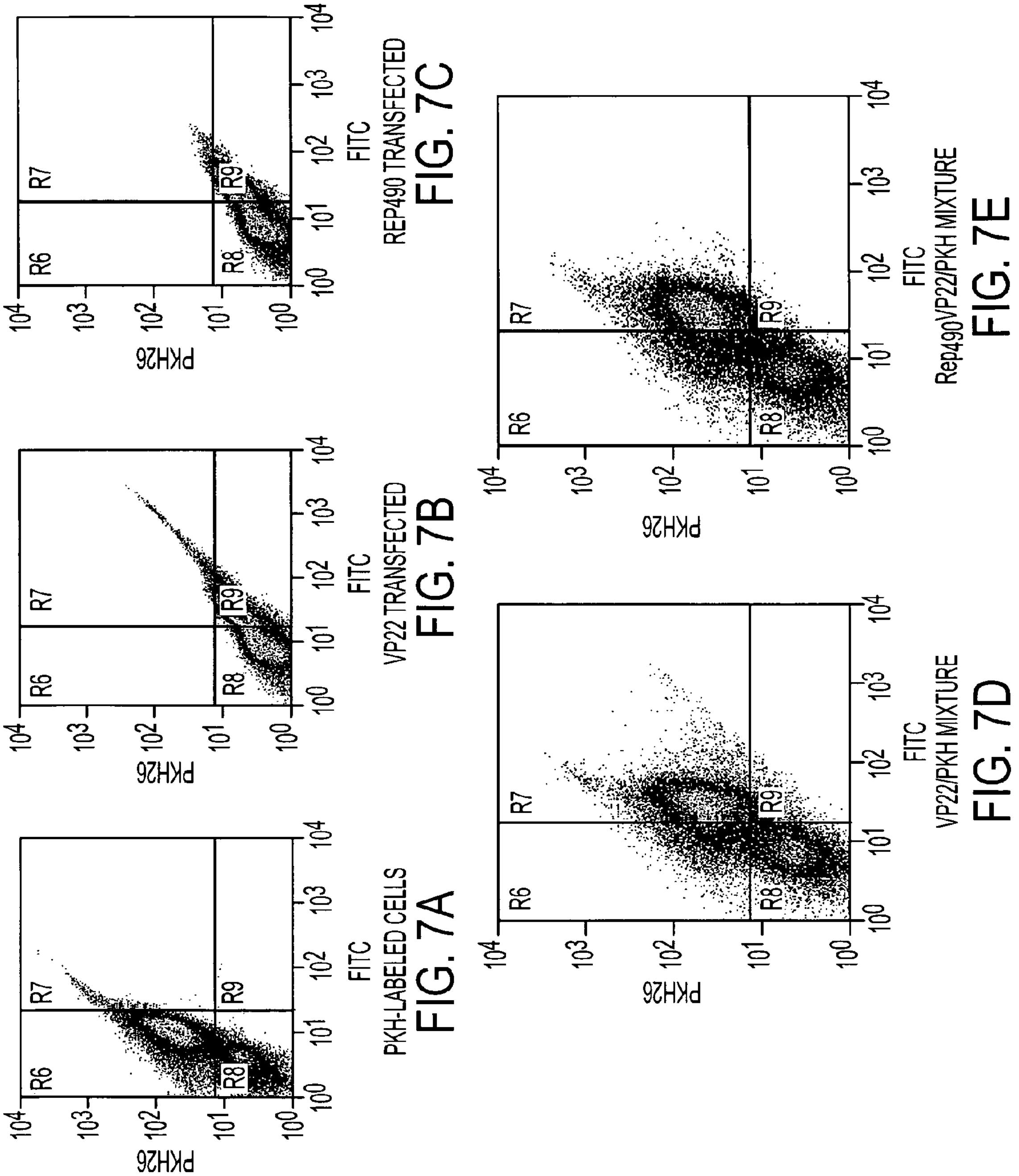
FIGS. 7A–7E present FACS analysis of trafficking of the AAVRep$_{490}$VP22 fusion protein.

To further confirm intercellular transport of Rep-VP22 fusions, 293 cells were transfected with expression plasmids encoding the Rep-VP22 fusion proteins and analyzed by flow cytometry. See FIG. 6. A separate culture of 293 cells was stained with PKH26, a vital membrane dye which permanently stains cells and is used for measuring cell division by flow cytometry. After expression of the VP22 protein for about 48 hours, these two populations of cells were mixed, incubated, and analyzed by flow cytometry using FITC conjugated anti fusion protein antibodies. Trafficking is indicated by demonstration of a cell population that stains with both PKH26 and antibody specific for VP22 in the VP22 fusion protein. The results are shown in FIG. 7. Panels A, B and C indicate that discrimination of PKH26 and antibody staining for VP22 or the VP22 fusions was comparatively specific. Analysis of cells after mixing (panels D and E) shows a comparatively large population of cells that is PHK26 and either VP22 or $AAVRep_{490}VP22$ double positive, indicating trafficking.

Example 5

Site-Specific Integration

An rAAV vector-containing plasmid pCWRHIVAPAP and a nucleic acid encoding one of the relevant Rep derivatives were cotransfected using calcium phosphate into $1.8\times10^6$ 293 cells seeded in 60 mm dishes. 293 cells were harvested between 60 and 90 hours posttransfection and washed twice with PBS at 4° C. Cell pellets were suspended in 100 mM NaCl, 25 mM EDTA, and 10 mM Tris, pH 8.0, with 1 μg/ml RNase A and incubated for 2 hours at 37° C. Sodium dodecyl sulfate (SDS) and Proteinase K then were added to a final concentration of 0.5% and 0.1 mg/ml, respectively, and the mixture was incubated overnight at 56° C. Genomic DNA was purified from the digested cell pellet material by phenol/chloroform extraction, followed by ammonium acetate/ethanol precipitation. Isolated DNA was quantified via spectrophotometric analysis. Similar experiments were performed using CWRHIVAPgkH, an rAAV vector encoding resistance to hygromycin. In these experiments, cells were grown in media supplemented with 250 μg/mL hygromycin and 400 μg/mL G418 to select for cells expressing the rAAV vector and fusion protein, respectively. Colonies resistant to both hygromycin and G418 were isolated and expanded. Genomic DNA was extracted from the cell lines as described above.

PCR analyses employing one primer within the vector and the other primer within AAVS1 were used to assess site-specific integration. Each 50 μl reaction contained 50 ng DNA template and 25 pmol each of a specific primer for rAAV vector and for AAVS1. Reaction mixtures were denatured at 95° C. for 5 minutes, cooled to 80° C. for 2 minutes (at which point the Taq polymerase was added), and then subjected to 35 cycles of amplification (94° C., 1 min; 55° C., 1 min; 72° C., 3 min), followed by a single extension cycle at 72° C. for 5 minutes.

To confirm rAAV vector site-specific integration into AAVS1, PCR products corresponding to vector cellular junction sequences were inserted into pGEM-T vectors (Promega, Madison, Wis.), amplified in DH5α cells, and subjected to agarose gel sequence analysis in two independent Southern analyses, one probed with an rAAV vector-specific (FIG. 9) and the other with an AAVS1-specific (FIG. 10) probe. PCR reactions were performed using the Taq DNA polymerase kit (Qiagen), designed to amplify DNA containing secondary structures following the manufacture's directions. Amplified products were separated using 0.8% agarose gel electrophoresis in duplicate, and transferred overnight to a nitrocellulose membrane according to methods known in the art. After cross-linking the DNA samples to the filter blot, the membrane was cut in half, each half containing a complete set of the samples to be analyzed. One blot half was hybridized with a random primed $^{32}P$-labeled AAV vector-specific probe while the other half was hybridized with a AAVS1-specific probe. Bands that were positive with both probes indicate site-specific integration. Western blots were used to confirm the different sizes of mutants. Phosphorimaging analysis (Molecular Dynamics) was used to evaluate the extent of rAAV vector integration. See FIG. 8.

Example 6 rAAV-Cell Junction Sequence Analysis

Preliminary DNA sequence alignment analyses of cell-vector junction sequences isolated following TA cloning of the junction fragment demonstrated both vector and AAVS1 sequences, indicating site-specific integration of the vector. See FIG. 11.

The invention claimed is:

1. A fusion polypeptide which comprises an adeno-associated virus 2 (AAV2) Rep protein sequence of the left open reading frame of the rep gene that lacks a functional nuclear localization signal sequence and a polypeptide sequence that confers nuclear localization on said fusion polypeptide.

2. A fusion polypeptide of claim 1, wherein said nuclear-localization-conferring polypeptide sequence is selected from the group consisting of Drosophila antennaepedia protein, human immunodeficiency virus-1 (HIV-1) tat protein, viral protein 22 (VP22), and functional fragments and variants thereof.

3. A fusion polypeptide of claim 1, wherein said nuclear-localizationconferring polypeptide sequence is selected from the group consisting of VP22 and functional fragments and variants thereof.

4. A fusion polypeptide of claim 1, wherein said Rep protein sequence contains a deletion mutation in the nuclear localization signal.

5. A fusion polypeptide of claim 1, wherein said Rep protein sequence is encoded by nucleotides 1883–3355 of SEQ ID NO:21.

6. A fusion polypeptide of claim 1, wherein said Rep protein sequence is encoded by nucleotides 1883–3352 of SEC ID NO:21.

7. A fusion polypeptide of claim 1, wherein said Rep protein sequence is encoded by nucleotides 1883–3349 of SEC ID NO:21.

8. A fusion polypeptide of claim 1, wherein said Rep protein sequence is encoded by nucleotides 1883–3346 of SEQ ID NO:21.

9. A fusion polypeptide of claim 1, wherein said Rep protein sequence is fused to the carboxyl terminus of said nuclear localization polypeptide sequence.

10. A fusion polypeptide of claim 1, wherein said Rep protein sequence is fused to the amino terminus of said nuclear localization polypeptide sequence.

11. A fusion polypeptide of claim 1, which further comprises a spacer of 4 to 7 amino acid residues between said Rep protein sequence and said nuclear localization polypeptide sequence.

12. A DNA construct encoding the fusion polypeptide of claim 1.

13. A DNA construct of claim 12 which further comprises a promoter.

14. A method for mediating site-specific integration of a rep-deleted recombinant adeno-associated virus (rAAV) vector into the genome of a cell which comprises transfecting said cell with a DNA construct of claim 13, expressing said DNA construct, and transfecting said cell with said rep-deleted recombinant adeno-associated virus (rAAV) vector.

15. A method for mediating site-specific integration of a rep-deleted recombinant adeno-associated virus vector to a cell which comprises transfecting said cell with said rep-deleted rAAV vector, and during said transfecting, contacting said cell with a fusion polypeptide of claim 1.

* * * * *

UNITED STATES PATENT AND TRADEMARK OFFICE
CERTIFICATE OF CORRECTION

PATENT NO. : 7,122,348 B2
APPLICATION NO. : 10/732813
DATED : October 17, 2006
INVENTOR(S) : Wong, Jr. et al.

It is certified that error appears in the above-identified patent and that said Letters Patent is hereby corrected as shown below:

Title Page: item (56);
Col. 1, cite no. 5, line 12, "Microtubles" should be --Microtubules--;

Col. 1, cite no. 6, line 16, "*Viroloy*" should be --Virology--;

Col. 1, cite no. 7, line 18, "Cells" should be --cells--;

Col. 1, cite no. 7, line 19, "*Therapu*" should be --*Therapy*"--;

Col. 1, cite no. 8, line 23, "onto" should be --into--;

Col. 2, cite no. 11, line 8, "Chromosone" should be --Chromosome--;

Col. 2, cite no. 12, line 12, "chromosone" should be --chromosome--;

Col. 2, cite no. 16, line 26, "1993" should be --1983--;

Col. 3, line 18, insert --.-- after "(B)";

Col. 4, line 6, "In" should be --in--;

Col. 4, line 20, delete first instance of "Table";

Col. 4, line 20, "SEC" should be --SEQ--;

Col. 5, line 57, "glydine" should be --glycine--;

Col. 6, line 16, "ORE" should be --ORF--;

Col. 8, line 67, "$AAV2REP_{490}VP22$" should be --$AAV2REP_{490}$-VP22--;

Col. 9, line 10, "plamids" should be --plasmids--;

Col. 9, line 28, "ORE" should be --ORF--;

Col. 9, line 37, "ORE" should be --ORF--;

Col. 11, line 15, "MEN" should be --MEM--;

Col. 12, line 4, "CFITC)" should be --(FITC)--;

UNITED STATES PATENT AND TRADEMARK OFFICE

CERTIFICATE OF CORRECTION

PATENT NO. : 7,122,348 B2
APPLICATION NO. : 10/732813
DATED : October 17, 2006
INVENTOR(S) : Wong, Jr. et al.

It is certified that error appears in the above-identified patent and that said Letters Patent is hereby corrected as shown below:

Col. 12, line 42, “posttransfection” should be --post-transfection--;

Col. 13, line 13, “manufacture’s” should be --manufacturer’s--;

In the Claims

Col. 48, line 62, “localizationconferring” should be --localization-conferring--.

Signed and Sealed this

Fourth Day of March, 2008

JON W. DUDAS
*Director of the United States Patent and Trademark Office*